(12) United States Patent
Casey et al.

(10) Patent No.: US 12,343,486 B2
(45) Date of Patent: *Jul. 1, 2025

(54) BALLOON CATHETER WITH VENTING OF RESIDUAL AIR IN A PROXIMAL DIRECTION

(71) Applicant: Neuravi Limited, Galway (IE)

(72) Inventors: Brendan Casey, Galway (IE); Karl Keating, Galway (IE); Ronald Kelly, Cannistown (IE); Barry O'Connell, Galway (IE)

(73) Assignee: NEURAVI LIMITED, Galway (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/159,081

(22) Filed: Jan. 24, 2023

(65) Prior Publication Data
US 2023/0173237 A1 Jun. 8, 2023

Related U.S. Application Data

(63) Continuation of application No. 16/601,221, filed on Oct. 14, 2019, now Pat. No. 11,607,531.
(Continued)

(51) Int. Cl.
*A61M 25/10* (2013.01)
*A61B 17/12* (2006.01)
(Continued)

(52) U.S. Cl.
CPC . *A61M 25/10185* (2013.11); *A61B 17/12109* (2013.01); *A61B 17/12136* (2013.01);
(Continued)

(58) Field of Classification Search
CPC ............ A61M 25/10185; A61M 25/10; A61M 25/104; A61M 25/0032; A61M 25/10181;
(Continued)

(56) References Cited

U.S. PATENT DOCUMENTS

| 4,188,954 A | 2/1980 | Patel et al. |
| 4,323,071 A | 4/1982 | Simpson et al. |

(Continued)

FOREIGN PATENT DOCUMENTS

| JP | S59-166163 A | 9/1984 |
| JP | S59-177064 A | 10/1984 |

(Continued)

OTHER PUBLICATIONS

Co-Pending, co-owned, U.S. Appl. No. 16/601,256, filed Oct. 14, 2019.
(Continued)

*Primary Examiner* — Brigid K Byrd
(74) *Attorney, Agent, or Firm* — TROUTMAN PEPPER LOCKE LLP

(57) ABSTRACT

A balloon guide catheter system including a balloon guide catheter having a catheter shaft that includes: (i) a main lumen; (ii) an inflation lumen; and (iii) an exhaust lumen. The terminating distal end of the inflation lumen and the terminating distal end of the exhaust lumen being in localized fluid communication with one another underneath the balloon while in a non-inflated state. A balloon is disposed about a distal region of an outer surface of the catheter shaft. The exhaust lumen is configured to purge the residual air in a proximal direction and out from a proximal region of the balloon guide catheter.

11 Claims, 17 Drawing Sheets

Related U.S. Application Data

(60) Provisional application No. 62/845,747, filed on May 9, 2019, provisional application No. 62/845,711, filed on May 9, 2019, provisional application No. 62/845,683, filed on May 9, 2019, provisional application No. 62/845,699, filed on May 9, 2019.

(51) Int. Cl.
    *A61M 39/22* (2006.01)
    *A61M 25/00* (2006.01)

(52) U.S. Cl.
    CPC ....... *A61M 39/223* (2013.01); *A61M 25/0032* (2013.01); *A61M 2025/0039* (2013.01); *A61M 25/005* (2013.01); *A61M 2025/0059* (2013.01); *A61M 25/0097* (2013.01); *A61M 25/1002* (2013.01); *A61M 2025/1061* (2013.01)

(58) Field of Classification Search
    CPC ........ A61M 39/223; A61M 2025/1061; A61M 2025/1077; A61M 2025/1043; A61M 2025/0037; A61M 2025/004
    See application file for complete search history.

(56) References Cited

U.S. PATENT DOCUMENTS

| | | | |
|---|---|---|---|
| 4,684,363 A * | 8/1987 | Ari | A61M 25/104 604/103.1 |
| 4,715,378 A | 12/1987 | Pope, Jr. et al. | |
| 4,753,238 A * | 6/1988 | Gaiser | A61M 25/104 606/195 |
| 4,793,351 A * | 12/1988 | Landman | A61M 25/10185 604/920 |
| 4,811,737 A | 3/1989 | Rydell | |
| 4,821,722 A | 4/1989 | Miller et al. | |
| 5,035,705 A | 7/1991 | Burns | |
| 5,100,385 A | 3/1992 | Bromander | |
| 5,135,486 A | 8/1992 | Eberle et al. | |
| 5,176,698 A | 1/1993 | Burns et al. | |
| 5,224,933 A * | 7/1993 | Bromander | A61M 25/104 604/256 |
| 5,256,143 A | 10/1993 | Miller et al. | |
| 5,800,421 A | 9/1998 | Lemelson | |
| 6,010,521 A | 1/2000 | Lee et al. | |
| 6,102,891 A | 8/2000 | Maria van Erp | |
| 6,102,931 A | 8/2000 | Thornton | |
| 6,517,515 B1 | 2/2003 | Eidenschink | |
| 6,709,429 B1 | 3/2004 | Schaefer et al. | |
| 6,811,559 B2 | 11/2004 | Thornton | |
| 6,953,431 B2 | 10/2005 | Barthel | |
| 6,994,687 B1 | 2/2006 | Shkolnik | |
| 7,160,266 B2 | 1/2007 | Shkolnik | |
| 7,163,503 B2 | 1/2007 | Toth | |
| 7,338,511 B2 | 3/2008 | Mirigian et al. | |
| 7,678,075 B2 | 3/2010 | Wantink et al. | |
| 8,298,218 B2 | 10/2012 | Mahrouche | |
| 8,926,560 B2 | 1/2015 | Dinh et al. | |
| 9,155,869 B2 | 10/2015 | Ehrenreich et al. | |
| 9,463,035 B1 | 10/2016 | Greenhalgh et al. | |
| 9,532,792 B2 | 1/2017 | Galdonik et al. | |
| 9,532,873 B2 | 1/2017 | Kelley | |
| 9,533,344 B2 | 1/2017 | Monetti et al. | |
| 9,539,011 B2 | 1/2017 | Chen et al. | |
| 9,539,022 B2 | 1/2017 | Bowman | |
| 9,539,122 B2 | 1/2017 | Burke et al. | |
| 9,539,382 B2 | 1/2017 | Nelson | |
| 9,549,830 B2 | 1/2017 | Bruszewski et al. | |
| 9,554,805 B2 | 1/2017 | Tompkins et al. | |
| 9,561,125 B2 | 2/2017 | Bowman et al. | |
| 9,572,982 B2 | 2/2017 | Burnes et al. | |
| 9,579,484 B2 | 2/2017 | Barnell | |
| 9,585,642 B2 | 3/2017 | Dinsmoor et al. | |
| 9,615,832 B2 | 4/2017 | Bose et al. | |
| 9,615,951 B2 | 4/2017 | Bennett et al. | |
| 9,622,753 B2 | 4/2017 | Cox | |
| 9,636,115 B2 | 5/2017 | Henry et al. | |
| 9,636,439 B2 | 5/2017 | Chu et al. | |
| 9,642,675 B2 | 5/2017 | Werneth et al. | |
| 9,655,633 B2 | 5/2017 | Leynov et al. | |
| 9,655,645 B2 | 5/2017 | Staunton | |
| 9,655,989 B2 | 5/2017 | Cruise et al. | |
| 9,662,129 B2 | 5/2017 | Galdonik et al. | |
| 9,662,238 B2 | 5/2017 | Dwork et al. | |
| 9,662,425 B2 | 5/2017 | Lilja et al. | |
| 9,668,898 B2 | 6/2017 | Wong | |
| 9,675,477 B2 | 6/2017 | Thompson | |
| 9,675,782 B2 | 6/2017 | Connolly | |
| 9,676,022 B2 | 6/2017 | Ensign et al. | |
| 9,692,557 B2 | 6/2017 | Murphy | |
| 9,693,852 B2 | 7/2017 | Lam et al. | |
| 9,700,262 B2 | 7/2017 | Janik et al. | |
| 9,700,399 B2 | 7/2017 | Acosta-Acevedo | |
| 9,717,421 B2 | 8/2017 | Griswold et al. | |
| 9,717,500 B2 | 8/2017 | Tieu et al. | |
| 9,717,502 B2 | 8/2017 | Teoh et al. | |
| 9,724,103 B2 | 8/2017 | Cruise et al. | |
| 9,724,526 B2 | 8/2017 | Strother et al. | |
| 9,750,565 B2 | 9/2017 | Bloom et al. | |
| 9,757,260 B2 | 9/2017 | Greenan | |
| 9,764,111 B2 | 9/2017 | Gulachenski | |
| 9,770,251 B2 | 9/2017 | Bowman et al. | |
| 9,770,577 B2 | 9/2017 | Li et al. | |
| 9,775,621 B2 | 10/2017 | Tompkins et al. | |
| 9,775,706 B2 | 10/2017 | Peterson et al. | |
| 9,775,732 B2 | 10/2017 | Khenansho | |
| 9,788,800 B2 | 10/2017 | Mayoras, Jr. | |
| 9,795,391 B2 | 10/2017 | Saatchi et al. | |
| 9,801,980 B2 | 10/2017 | Karino et al. | |
| 9,808,599 B2 | 11/2017 | Bowman et al. | |
| 9,833,252 B2 | 12/2017 | Sepetka et al. | |
| 9,833,604 B2 | 12/2017 | Lam et al. | |
| 9,833,625 B2 | 12/2017 | Waldhauser et al. | |
| 10,576,254 B2 | 3/2020 | Yang et al. | |
| 10,682,152 B2 | 6/2020 | Vale et al. | |
| 11,202,891 B2 | 12/2021 | Gulachenski et al. | |
| 11,571,553 B2 | 2/2023 | Keating et al. | |
| 11,931,522 B2 | 3/2024 | Kelly et al. | |
| 2001/0049464 A1 | 12/2001 | Ganz | |
| 2002/0087156 A1 | 7/2002 | Maguire et al. | |
| 2002/0103473 A1 | 8/2002 | Roychowdhury et al. | |
| 2003/0023204 A1 | 1/2003 | Vo et al. | |
| 2003/0120207 A1 | 6/2003 | Wang | |
| 2004/0260329 A1 | 12/2004 | Gribbons et al. | |
| 2005/0070881 A1 | 3/2005 | Gribbons et al. | |
| 2005/0124932 A1 | 6/2005 | Foster et al. | |
| 2005/0182359 A1 | 8/2005 | Chin et al. | |
| 2006/0030814 A1 | 2/2006 | Valencia et al. | |
| 2007/0010847 A1 | 1/2007 | Pepper | |
| 2008/0147048 A1 | 6/2008 | Deutsch | |
| 2008/0200904 A1 * | 8/2008 | Cluff | A61M 25/00 604/537 |
| 2010/0234940 A1 | 9/2010 | Dolan | |
| 2010/0324534 A1 | 12/2010 | Hudson et al. | |
| 2012/0143239 A1 | 6/2012 | Aklog et al. | |
| 2012/0265134 A1 | 10/2012 | Echarri et al. | |
| 2012/0296366 A1 | 11/2012 | Rundquist et al. | |
| 2013/0289549 A1 | 10/2013 | Nash et al. | |
| 2014/0155980 A1 | 6/2014 | Turjman et al. | |
| 2014/0188043 A1 | 7/2014 | Shibahara | |
| 2014/0257359 A1 | 9/2014 | Tegels et al. | |
| 2014/0276028 A1 | 9/2014 | Stigall et al. | |
| 2015/0032049 A1 | 1/2015 | Hopkinson et al. | |
| 2015/0057536 A1 | 2/2015 | Stigall et al. | |
| 2015/0073467 A1 | 3/2015 | Eaton | |
| 2015/0174363 A1 | 6/2015 | Sutermeister et al. | |
| 2015/0224290 A1 | 8/2015 | Chanduszko et al. | |
| 2015/0265329 A1 | 9/2015 | Lalonde et al. | |
| 2016/0001040 A1 | 1/2016 | Yamaguchi et al. | |
| 2017/0007264 A1 | 1/2017 | Cruise et al. | |
| 2017/0007265 A1 | 1/2017 | Guo et al. | |
| 2017/0020670 A1 | 1/2017 | Murray et al. | |
| 2017/0020700 A1 | 1/2017 | Bienvenu et al. | |

(56) References Cited

U.S. PATENT DOCUMENTS

| | | |
|---|---|---|
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Grandfield |
| 2017/0100183 A1 | 4/2017 | Iaizzo et al. |
| 2017/0113023 A1 | 4/2017 | Steingisser et al. |
| 2017/0135709 A1 | 5/2017 | Nguyen et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1* | 12/2017 | Guyon ............ A61M 25/10187 |
| 2018/0236203 A1 | 8/2018 | Franklin et al. |
| 2018/0333192 A1 | 11/2018 | Sliwa et al. |
| 2019/0167287 A1 | 6/2019 | Vale et al. |
| 2019/0167955 A1 | 6/2019 | Panian |
| 2019/0359786 A1 | 11/2019 | Trahan et al. |
| 2020/0179657 A1 | 6/2020 | Liu |
| 2020/0246036 A1 | 8/2020 | Kallmes et al. |
| 2020/0384242 A1 | 12/2020 | Havard et al. |
| 2022/0143360 A1 | 5/2022 | Kugler et al. |

FOREIGN PATENT DOCUMENTS

| | | |
|---|---|---|
| JP | S63-95065 A | 4/1988 |
| JP | S63-158064 A | 7/1988 |
| JP | S64-017659 A | 1/1989 |
| JP | 2014-124393 A | 7/2014 |
| JP | 2016168151 | 9/2016 |
| WO | 2007139799 | 12/2007 |
| WO | 2013163254 | 10/2013 |
| WO | 2017192999 | 11/2017 |

OTHER PUBLICATIONS

Co-Pending, co-owned, U.S. Appl. No. 16/601,185, filed Oct. 14, 2019.

Co-Pending, co-owned, U.S. Appl. No. 16/601,202, filed Oct. 14, 2019, now U.S. Pat. No. 11,571,553.

L.E. Romans, "The Use of Contrast Media in the CT Department", CEWebsource.com, May 15, 2013 (50 pp).

Japanese Office Action dated Jul. 9, 2024, in corresponding JP Appln. No. 2020-083087.

English Translation of Japanese Office Action dated Jul. 9, 2024, in corresponding JP Appln. No. 2020-083087.

* cited by examiner

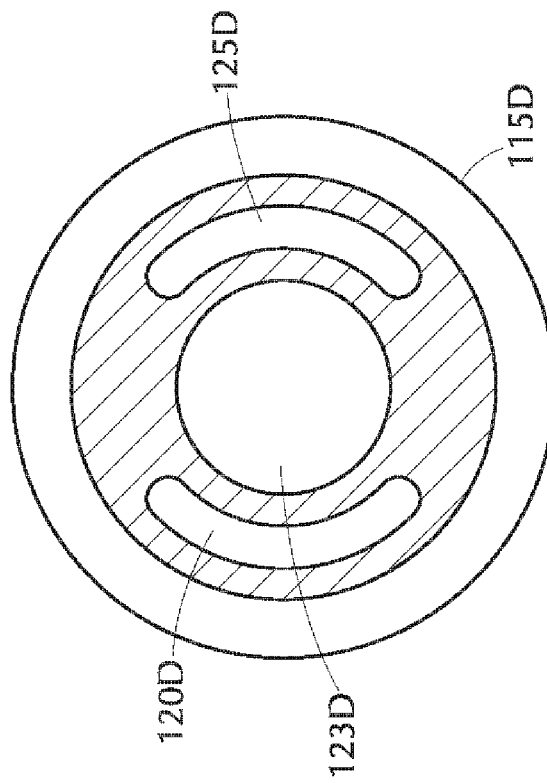
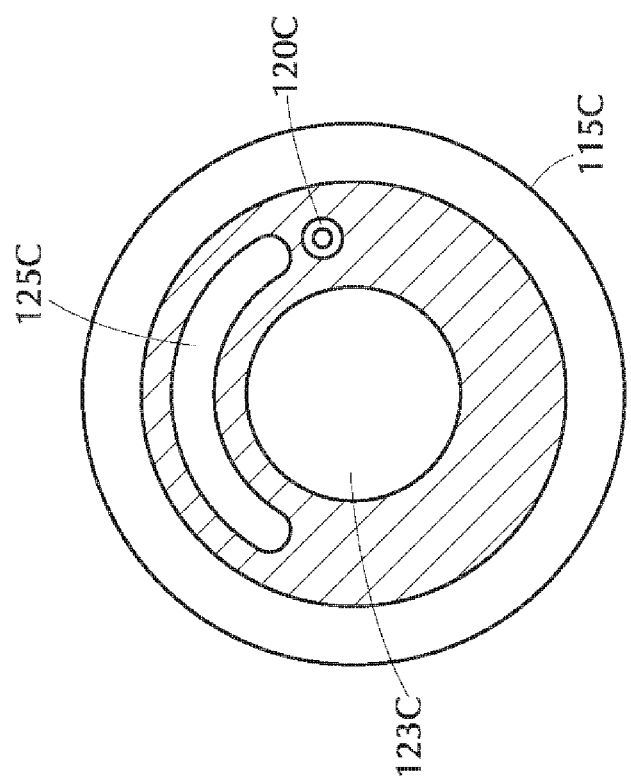

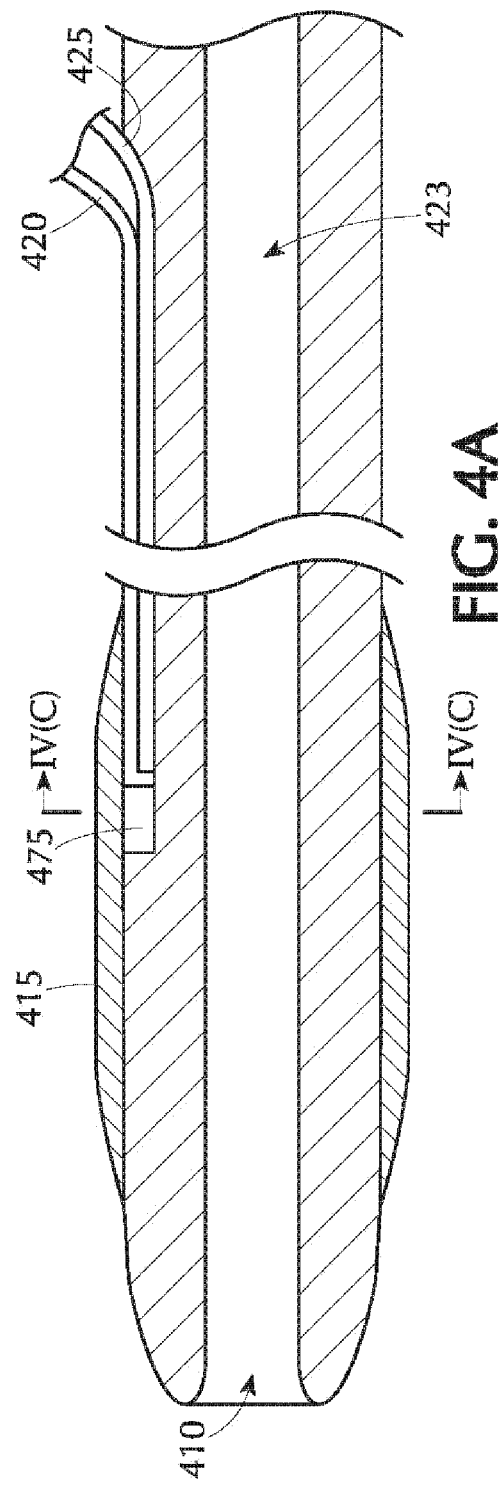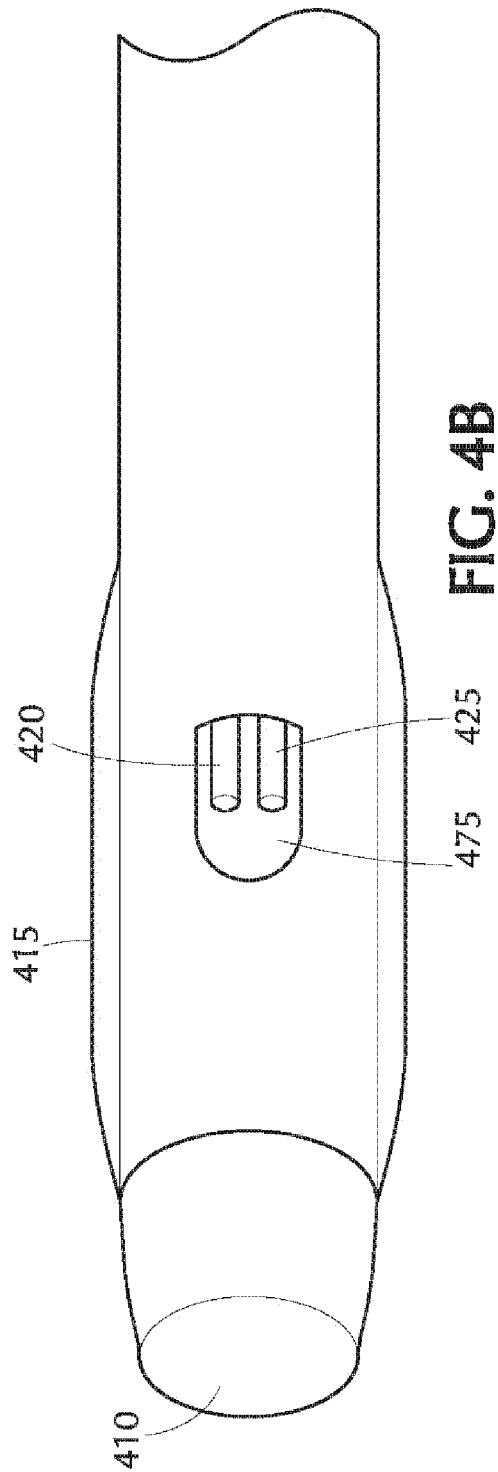

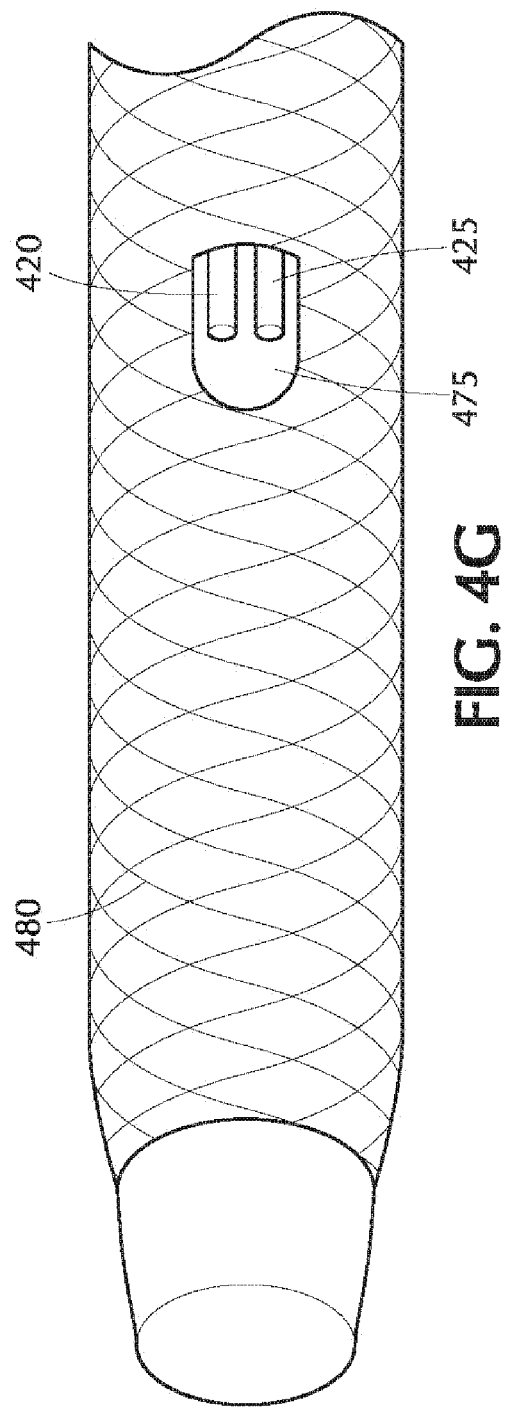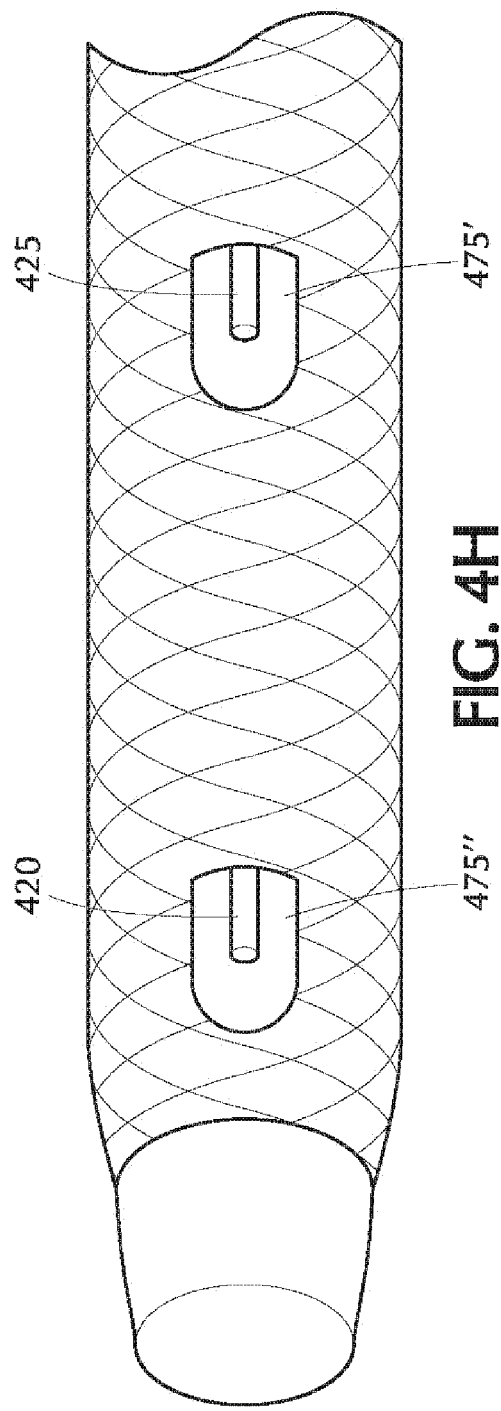

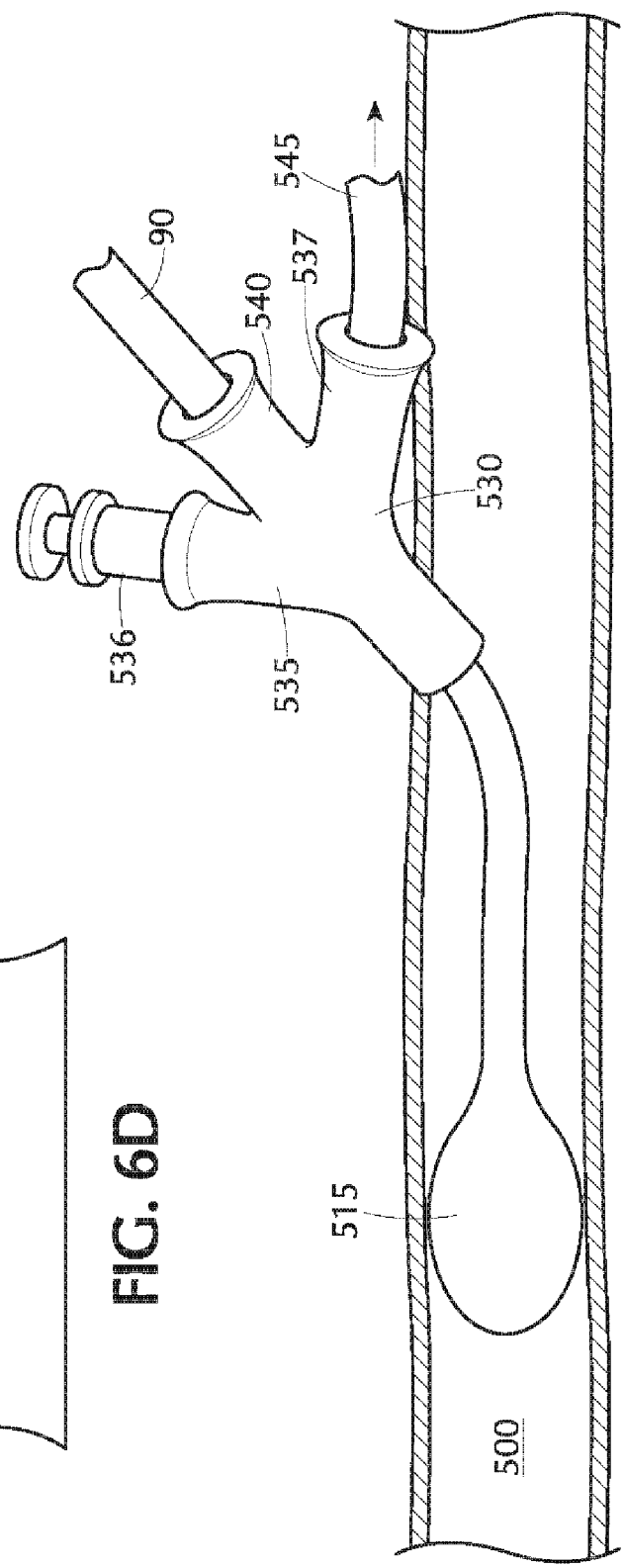
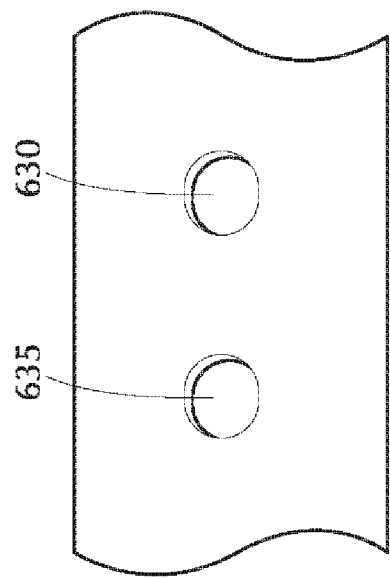

BALLOON CATHETER WITH VENTING OF RESIDUAL AIR IN A PROXIMAL DIRECTION

CROSS-REFERENCE TO RELATED APPLICATIONS

This application is a continuation of U.S. Ser. No. 16/601,221, filed on Oct. 14, 2019, which claims the benefit of the following: U.S. Provisional Application No. 62/845,683, filed on May 9, 2019; U.S. Provisional Application No. 62/845,699, filed on May 9, 2019; U.S. Provisional Application No. 62/845,711, filed on May 9, 2019; and U.S. Provisional Application No. 62/845,747, filed on May 9, 2019, each of which is herein incorporated by reference in its entirety.

BACKGROUND OF THE INVENTION

Field of the Invention

The present invention relates to an intravascular medical system. In particular, the present invention is directed to an improved balloon catheter with venting of residual air in a proximal direction.

Description of Related Art

Balloon catheters are widely used in connection with a variety of intravascular medical procedures or treatments. Typically, a fluid or liquid under pressure is injected into an inflation lumen of the catheter in order to inflate the balloon. Prior to being introduced into the body, the balloon catheter is prepped by the physician or interventionalist correctly following a multi-step process to properly purge residual air from the inflation lumen and balloon. Specifically, the purging of air from the inflation lumen prevents an air embolism from entering the vasculature system in the case of leak or rupture of the balloon. Furthermore, residual air is also purged from the balloon itself to insure inflation of the balloon using a desired volume of inflation medium that might otherwise be inaccurate due to the compressed unknown volume of residual air within the balloon.

One common technique for purging residual air from a balloon catheter prior to introduction into the body is by applying a vacuum or negative pressure to the proximal end of the inflation lumen using a syringe or vacuum and drawing out as much air as possible proximally through the inflation lumen. Then the syringe vacuum is closed off via a valve (e.g., a three-way luer valve) and the inflation lumen is opened under vacuum allowing the dispensing of the inflation medium therethrough and into the balloon. During injection of the inflation medium, the balloon is preferably held vertically with a downward inclination to promote air to exhaust allowing the residual air within the catheter to rise through the inflation medium towards an inflation port. The inflation medium and some air bubbles are withdrawn from the catheter, and additional inflation medium is again injected. It is not uncommon for these steps to have to be repeated multiple times to adequately purge the catheter of the residual air, requiring a substantial amount of preparation time. With each iteration these steps must be correctly followed.

In angiographic balloon catheter systems, the device is configured so that the residual air from the inflation lumen and balloon is exhausted via a distal vent, rather than proximally.

Since the prepping steps are numerous and time consuming, physicians and interventionalist may be discouraged from using the device altogether. Those physicians or interventionalist that use the device, may unintentionally omit from following the proper prepping steps or do so improperly after introducing the balloon catheter into the body resulting in potential health risks to the patient.

It is therefore desirable to design an improved balloon catheter and method for use of such improved balloon catheter with venting of residual air in a proximal direction while minimizing the steps associated therewith thereby promoting use of the device.

SUMMARY OF THE INVENTION

An aspect of the present invention relates to an improved balloon catheter with venting of residual air in a proximal direction.

Another aspect of the present invention is directed to a balloon guide catheter system including a balloon guide catheter. The balloon guide catheter has a catheter shaft with a proximal end and an opposite distal end; wherein the catheter shaft includes: (i) a main lumen defined axially through the catheter shaft; (ii) an inflation lumen extending axially along the catheter shaft; the inflation lumen having a proximal end, an opposite terminating distal end; and (iii) an exhaust lumen extending axially along the catheter shaft, the exhaust lumen having a proximal end and an opposite terminating distal end. The terminating distal end of the inflation lumen and the terminating distal end of the exhaust lumen are in localized fluid communication with one another underneath the balloon while in a non-inflated state. In addition, the balloon guide catheter further includes a balloon disposed about a distal region of an outer surface of the catheter shaft, wherein the exhaust lumen is configured to purge the residual air in a proximal direction and out from a proximal region of the balloon guide catheter.

Still another aspect of the present invention is directed to a method for using a balloon guide catheter system as described in the preceding paragraph. The method including the step of dispensing an inflation medium through an inflation port of a hub connected to the proximal end of the catheter shaft and into the inflation lumen. The inflation medium is advanced distally through the inflation lumen pushed by the dispensed inflation medium, causing the residual air to be exhausted proximally through the exhaust lumen exiting from the terminating distal end of the inflation lumen. The residual air being expelled through a membrane permitting passage therethrough of only the residual air and out from a proximal region of the balloon guide catheter.

BRIEF DESCRIPTION OF THE DRAWING

The foregoing and other features of the present invention will be more readily apparent from the following detailed description and drawings illustrative of the invention wherein like reference numbers refer to similar elements throughout the several views and in which:

FIGS. 3A-3D depict radial cross-sectional views of different exemplary configurations of the exhaust and inflation lumen in the present inventive balloon catheter along lines in FIG. 1B;

FIG. 4A is a partial axial cross-sectional view of the distal end of the present inventive catheter with the balloon in a deflated state taut against the outer surface of the catheter shaft, wherein terminating distal ends of the respective inflation and exhaust lumen coincide within a single D-shape localized fluid communication channel defined in the outer wall of the catheter shaft;

FIG. 4B is a top view of the catheter in FIG. 4A;

FIG. 4G is a top view of the distal end of the present inventive catheter with the balloon in a deflated (non-inflated) state, wherein terminating distal ends of the respective inflation and exhaust lumens coincide within a single localized fluid communication channel defined in the outer wall of the catheter shaft and a surface profile disposed about a portion of the outer surface of the catheter shaft;

FIG. 4H is a top view of the distal end of the present inventive catheter with the balloon in a deflated (non-inflated) state, wherein terminating distal ends of the respective inflation and exhaust lumens are staggered relative to one another so that the terminating distal end of the inflation lumen coincides with a first localized fluid communication channel, while the terminating distal end of the exhaust lumen coincides with a second localized fluid communication channel spaced apart in an axial direction from the first localized fluid communication channel;

FIG. 5 is a perspective view of the present inventive balloon catheter advanced to a target site within a vessel of the body;

FIG. 6D is a top view of a portion of the balloon catheter of FIG. 6A with the balloon removed depicting the arrangement of the inlet and outlet ports in the catheter shaft;

DETAILED DESCRIPTION OF THE INVENTION

The terms "distal" or "proximal" are used in the following description with respect to a position or direction relative to the treating physician or medical interventionalist. "Distal" or "distally" are a position distant from or in a direction away from the physician or interventionalist. "Proximal" or "proximally" or "proximate" are a position near or in a direction toward the physician or medical interventionalist. The terms "occlusion", "clot" or "blockage" are used interchangeably.

The present inventive balloon catheter has multiple lumens arranged in the outer wall of the catheter radially outward relative to a main lumen that receives a guidewire therethrough. Specifically, there is at least one inflation lumen and at least one exhaust/venting lumen, each extending axially in the outer wall of the catheter from the hub to the balloon. Respective distal ends of the inflation lumen and exhaust/venting lumen are in localized fluid communication with one another. The diameter size of the main lumen of the device is sufficient to serve as a conduit for guidewire(s) (e.g., 0.014", 0.018", 0.035" & 0.038" guidewires) as well as ancillary devices such as; accommodating microcatheters, mechanical thrombectomy devices, diagnostic catheters, intermediate catheters/aspiration catheters during the procedure. Preferably, the main lumen has a diameter of approximately 0.088".

Regardless of the particular configuration, the present inventive balloon catheter purges, exhaust or vents residual air in a proximal direction from the balloon catheter.

Figure 1A:
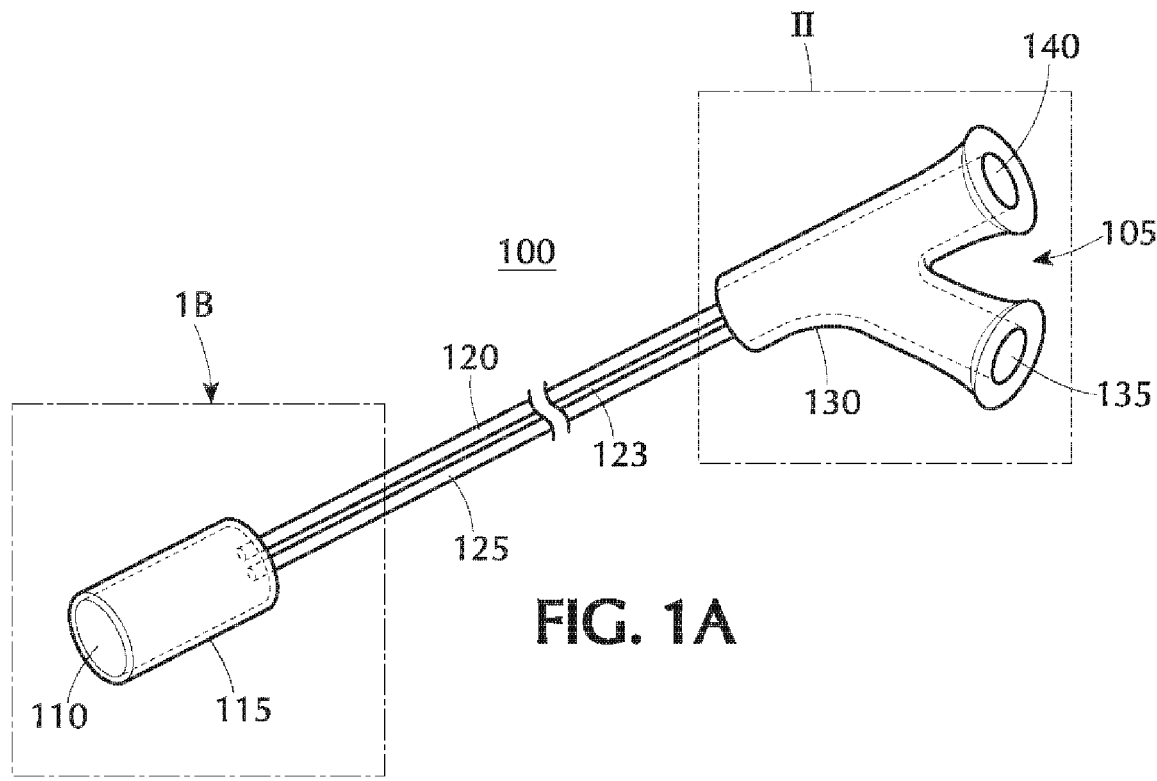
FIG. 1A is a perspective view of the balloon catheter in accordance with the present invention.

Referring to the perspective view of the present inventive balloon catheter 100 depicted in FIG. 1A, the catheter has a proximal end 105 and an opposite distal end 110. A hub 130 is secured proximate the proximal end 105 of the balloon catheter 100. In a first configuration illustrated in FIG. 1A, hub 130 includes a main/guidewire port 140 for receiving therein a guidewire 90 or ancillary device. A separate inflation medium port 135 is also provided in the hub 130 for receiving therein inflation medium (e.g., preferably, a 50% contrast saline solution) introduced into the balloon catheter 100 from a syringe or other dispensing mechanism (syringe 536 is shown in FIG. 5). In the configuration shown in FIG. 1A, hub 130 does not have an exhaust or vent port. Rather, residual air is vented or exhausted via an aperture defined in the exterior surface of the exhaust lumen proximate the proximal end of the catheter shaft, but distally of the hub 130. While in a deflated (non-inflated) state, balloon 115 fits tightly around the catheter shaft prohibiting residual air from being present between the deflated balloon and catheter shaft. Distal terminating ends of both the inflation lumen 125 and exhaust lumen 120 coincide beneath the balloon 115 and are arranged close to one another so that the relatively low volume residual air in the inflation lumen communicates effectively to the exhaust lumen. The progressing inflation medium follows the path of least resistance flowing into the balloon region rather than advancing back up the exhaust lumen.

Figure 1B:
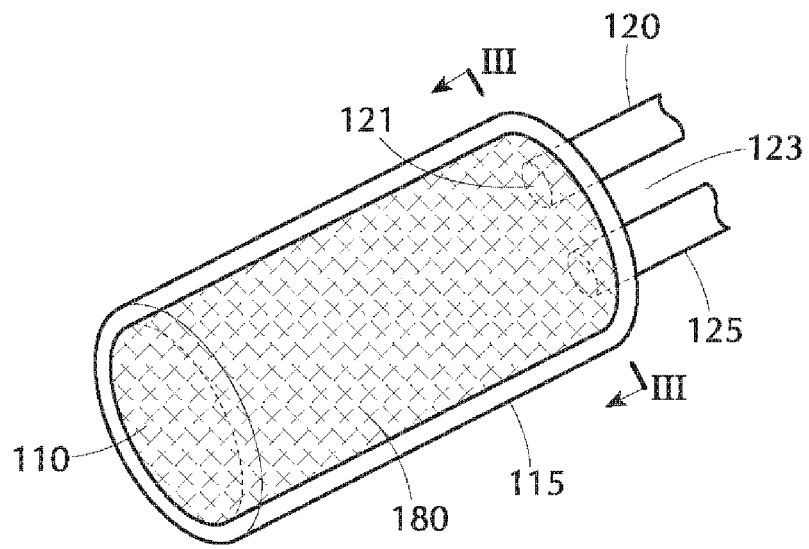
FIG. 1B is an enlarged view of the dashed square area 1B of the balloon portion of the balloon catheter of FIG. 1A depicting the mesh surface profile beneath the balloon that promotes fluid communication between the inflation and exhaust lumen.

Arranged axially or longitudinally through the balloon catheter 100 starting from the proximal end 105 are at least three separate, distinct, independent lumen, namely a main/guidewire lumen 123, an exhaust lumen 120 and an inflation lumen 125. The exhaust and inflation lumen 120, 125 are arranged radially outward relative to the main/guidewire lumen 123. In addition, the main/guidewire lumen 123 extends from the proximal end 105 to the opposite distal end 110, while respective terminating distal ends of the exhaust lumen 120 and inflation lumen 125 terminate beneath the balloon 115 (coincide with the balloon), as is clearly visible from the enlarged partial view of the distal end of the catheter in FIG. 1B.

Preferably, proximate the terminating distal end of the exhaust lumen 120 is a microporous membrane or filter 121. Pores of the microporous membrane are sized to permit only the passage of gas (e.g., residual air) therethrough, liquid (inflation medium) dispensed through the inflation lumen is prevented from permeating through the microporous membrane allowing the pressure within the inflation lumen to build-up and inflate the balloon as the volume within the balloon fills with the inflation medium. Preferably, the microporous membrane is a certain grade (based on porosity and thickness) of sintered polytetrafluoroethylene (PTFE), for example, expanded polytetrafluoroethylene (ePTFE) that permits the passage of air molecules therethrough but acts as a barrier to larger higher cohesive molecules such as water and contrast agent. Such microporous membrane may also prevent air-locking of the exhaust lumen and improper operation of the catheter.

Figure 2A:
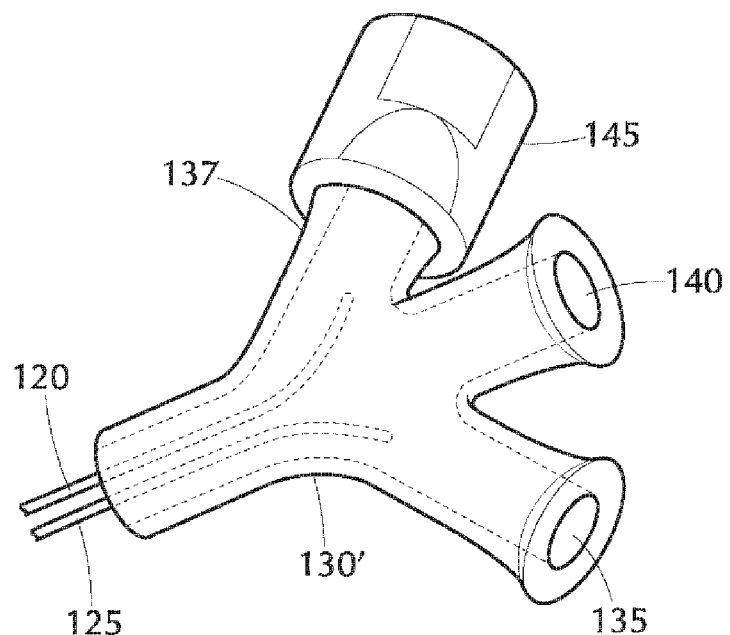
FIG. 2A is an alternative hub portion configuration (dashed square area II) of the balloon catheter of FIG. 1A with a 1-way valve attached to the exhaust port of the hub.
Figure 2B:
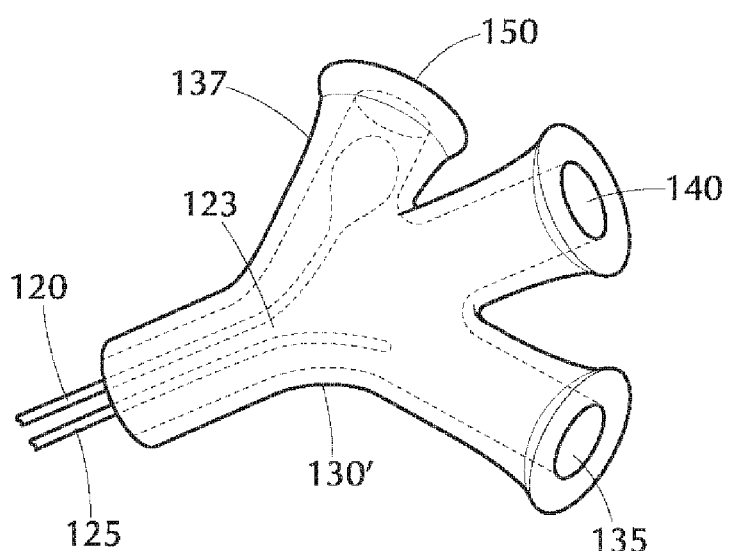
FIG. 2B is still another hub portion configuration (dashed square area II) of the balloon catheter of FIG. 1A with a purge lung serving as the exhaust port of the hub.

FIG. 2A is an alternative configuration of the hub 130' which includes an exhaust port 137 (through which the residual air purged in a proximal direction exits from the balloon catheter 100) as well as the previously described inflation port 135 and main/guidewire port 140. Different ancillary devices are connectable to the exhaust port 137. In one exemplary embodiment depicted in FIG. 2A, a 1-way valve 145 may be connected to the exhaust port 137 to control expelling the residual air from the balloon catheter. An alternative configuration is shown in FIG. 2B wherein the exhaust port 137 has been replaced by an inflatable lung, container or sac 150 to store therein the residual air that has been proximally purged from the balloon catheter.

In operation of the present inventive balloon catheter, inflation medium (preferably, 50% contrast saline solution) is introduced into the catheter using a syringe or other dispensing device attached to the inflation port of the hub. The inflation medium travels through the inflation lumen and into the deflated balloon. A microporous membrane located at the interface of the balloon and exhaust lumen has pores that are sized to prohibit the passage therethrough of the inflation medium, allowing only the residual air to pass out of the balloon and through the exhaust lumen. As the balloon fills with the inflation medium it inflates. Coinciding with the inflation of the balloon, the pressure inside the balloon increases causing the residual air in the balloon to be automatically exhausted or vented in a proximal direction through the exhaust lumen. At the hub, the residual air exiting from the balloon catheter may be controlled using a sealable 1-way exhaust valve and/or the purged residual air can be stored in an inflatable or expandable purge lung thereby removing the residual air from the system and storing it outside of the body in the hub by taking advantage of the fact that it is compressible.

By way of non-limiting example, numerous configurations of one or more exhaust lumen and one or more inflation lumen, each arranged radially outward from the main lumen in the balloon catheter 100 are shown and described. Additional configurations are possible and within the intended scope of the present invention with the common feature among the different configurations that the residual air is exhausted through the exhaust lumen in a proximal direction, rather than in a distal direction, from the catheter. Several exemplary designs of the exhaust and inflation lumen as well as their arrangement relative to one another in the balloon catheter are illustrated in FIGS. 3A-3D. In FIG.

Figure 3B:
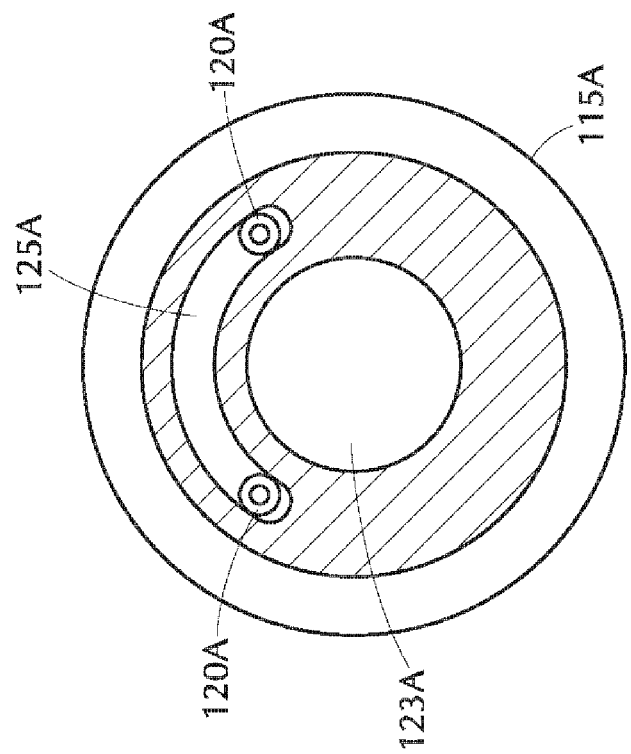
Figure 3A:
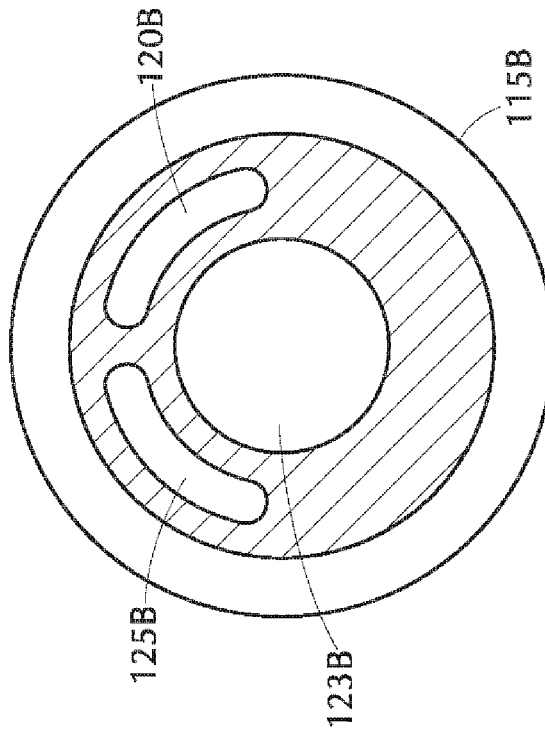

3A, the inflation lumen 125A has a curved segment radial cross-section whose radius of curvature shares a common center (coaxial; concentric) with that of the main/guidewire lumen 123A. Two exhaust lumen 120A having a circular radial cross-section are illustrated radially displaced from one another as far as possible within the inflation lumen 125A, but any number of one or more exhaust lumen may be provided, as desired, as well as the location or spacing of the exhaust lumen(s) 120A within the inflation lumen 125A. FIG. 3B is an alternative configuration wherein each of the exhaust and inflation lumens 120B, 125B, respectively, has a curved segment radial cross-section whose radius of curvature shares a common center (coaxial; concentric) with that of the main/guidewire lumen 123B. Yet another configuration is depicted in FIG. 3C. Similar to FIG. 3A, the inflation lumen 125C in FIG. 3C has a curved segment radial cross-section whose radius of curvature shares a common center (coaxial; concentric) with that of the main/guidewire lumen 123C. However, in this particular design a single exhaust lumen 120C is separate, distinct and independent of the inflation lumen 125C (not disposed within the inflation lumen, as in FIG. 3A). While still another possible configuration is illustrated in FIG. 3D. Like that of FIG. 3B, each of the exhaust and inflation lumens 120D, 125D, respectively, in FIG. 3D has a curved segment radial cross-section whose radius of curvature shares a common center (coaxial; concentric) with that of the main/guidewire lumen 123A. FIG. 3D differs from FIG. 3B in that the exhaust and inflation lumen 120D, 125D, respectively, are arranged approximately 180 degrees radially separated from one another (mirror images of one another). In another embodiment the curved inflation and exhaust lumens may be 'D' shaped or have a smaller/larger radius or curvature than that of the main/guidewire lumen. These are only non-limiting illustrative examples of different arrangements of the main, exhaust and inflation lumens in the catheter.

FIG. 4A is an exemplary partial axial cross-sectional view of the respective distal ends of an exhaust lumen 420 and inflation lumen 425 coinciding with the balloon 415, wherein the balloon is shown in a deflated (non-inflated) state. A localized fluid communication channel, basin or recess 475 is defined in the outer wall of the catheter shaft in a location anywhere in an axial direction that coincides with the balloon (e.g., proximal region of the balloon, mid region of the balloon, distal region of the balloon) so long as the channel is beneath/underneath (coincides with) the balloon 415. As is clearly visible from the top view in FIG. 4B, the localized fluid communication channel 475 may be D-shape, however, other geometric shapes (e.g., circle, oval, etc.) are contemplated. Fluid communication between terminating distal ends of the respective inflation lumen 425 and exhaust/vent lumen 420 occurs within this localized fluid communication channel 475. In FIG. 4B, the terminating distal ends of the respective exhaust and inflation lumen extend partially into the localized fluid communication channel 475. Alternatively, the terminating distal ends of the respective exhaust and inflation lumen may coincide with the perimeter or interface of the localized communication channel 475. FIG. 4C is a radial cross-sectional view through the localized fluid communication channel 475 along lines IV(C)-IV(C) of FIG. 4A depicting the side-by-side configuration of the terminating distal ends of the respective inflation and exhaust lumens 425, 420 therein. While in a deflated (non-inflated) state, balloon 415 is taut around the outer surface of the catheter shaft, as shown in FIG. 4A. As a result, following the path of least resistance, the residual air advanced through the inflation lumen 425 by the pressurized injected inflation medium is expelled proximally through the exhaust lumen 420 and from the catheter, without inflating the balloon 415.

Figure 4D:
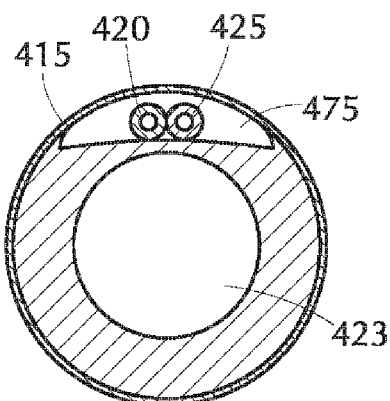
FIGS. 4D-4F are alternative exemplary radial cross-sectional views through the localized fluid communication channel showing different arrangements of the terminating distal ends of the respective inflation and exhaust lumen that coincide within a single localized fluid communication channel defined in an outer wall of the catheter shaft.
Figure 4E:
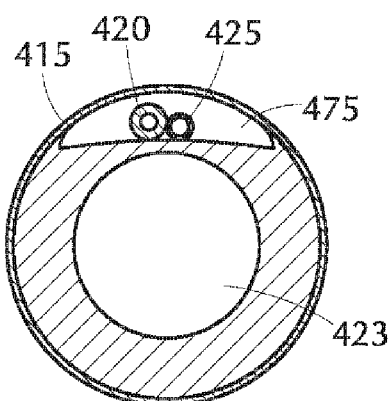
Figure 4C:
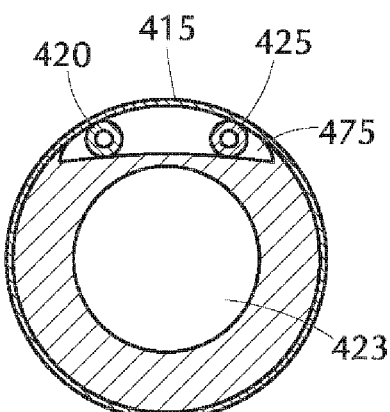
FIG. 4C is a radial cross-sectional view through the localized fluid communication channel of FIG. 4A alone lines IV(C)-IV(C)
Figure 4K:
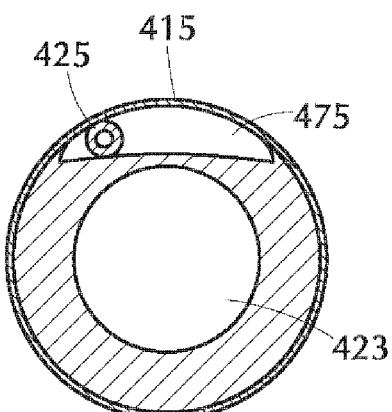
FIG. 4K is a radial cross-sectional view through the localized fluid communication channel of FIG. 4I along lines IV(K)-IV(K) showing the inflation lumen coinciding within a single localized fluid communication channel defined in an outer wall of the catheter shaft.
Figure 4F:
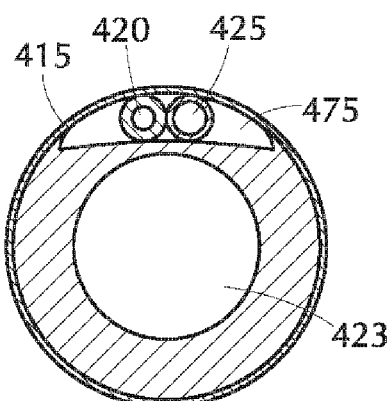

Alternative arrangements or configurations of the terminating distal ends of the respective exhaust and inflation lumen within the localized fluid communication channel 475 radially outward from the main/guidewire lumen 423 are depicted in the different radial cross-sectional views in FIG. 4D-4F. Addressing each separately, in FIG. 4D, inflation lumen 425 and exhaust lumen 420 are side-by-side in physical contact with one another and equal both in inner and outer diameters. FIG. 4E illustrates again a side-by-side arrangement with the two lumens in physical contact with one another within the localized fluid communication channel 475, however, the lumen differ in both inner and outer diameters. Specifically, the outer diameter of inflation lumen 425 is smaller than the outer diameter of the exhaust lumen 420, but the inner diameter of the inflation lumen 425 is larger than the inner diameter of the exhaust lumen 420. Preferably, the inner diameter of the inflation lumen is greater than the inner diameter of the exhaust lumen since the exhaust lumen merely functions to exhaust the residual air. In the arrangement in FIG. 4F, the inflation and exhaust lumens 425, 420 again are disposed side-by-side in physical contact with one another within the localized fluid communication channel 475. The outer diameters of the inflation and exhaust lumen are equal in diameter, while the inner diameter of the inflation lumen 425 is greater than that of the exhaust lumen 420. Any combination or permutation of these arrangements of the exhaust and inflation lumens within the channel as well as the sizes of the inner and outer diameters of each lumen is within the scope of the invention.

FIG. 4G is a top view of a partial distal section of still another configuration of the present inventive balloon catheter having a single localized fluid communication channel defined in the shaft in which distal terminating ends of respective exhaust and inflation lumen coincide within the single localized fluid communication channel. Disposed about a portion of the outer perimeter of the catheter shaft is a surface profile 480 that coincides with the localized fluid communication channel 475 to promote the flow of fluid from the inflation lumen 425 to the exhaust lumen 420. Preferably, the surface profile 480 is a mesh made of polymeric, metal and/or other material wrapped about the outer surface of the catheter shaft. The balloon extends axially so as to completely cover or enclose the surface profile 480. A radial cross-sectional profile through the single localized fluid communication channel 475 would be similar to that illustrated in FIG. 4C, although different arrangements such as those shown in FIGS. 4D-4F are possible, as desired.

FIG. 4H is a top view of still another configuration in which the terminating distal end of the inflation lumen 425 coincides with a first localized fluid communication channel 475', while the terminating distal end of the exhaust lumen 420 coincides with a second localized fluid communication channel 475" displaced axially apart from the first localized fluid communication channel 475'. In this arrangement, the surface profile 480 coincides with both the first and second localized fluid communication channels 475', 475". Once again, the surface profile 480 promotes fluid communication between inflation and exhaust lumens which is particularly applicable in this arrangement wherein the first and second localized fluid communication channels 475', 475" are displaced axially from one another along the catheter shaft.

Figure 4I:
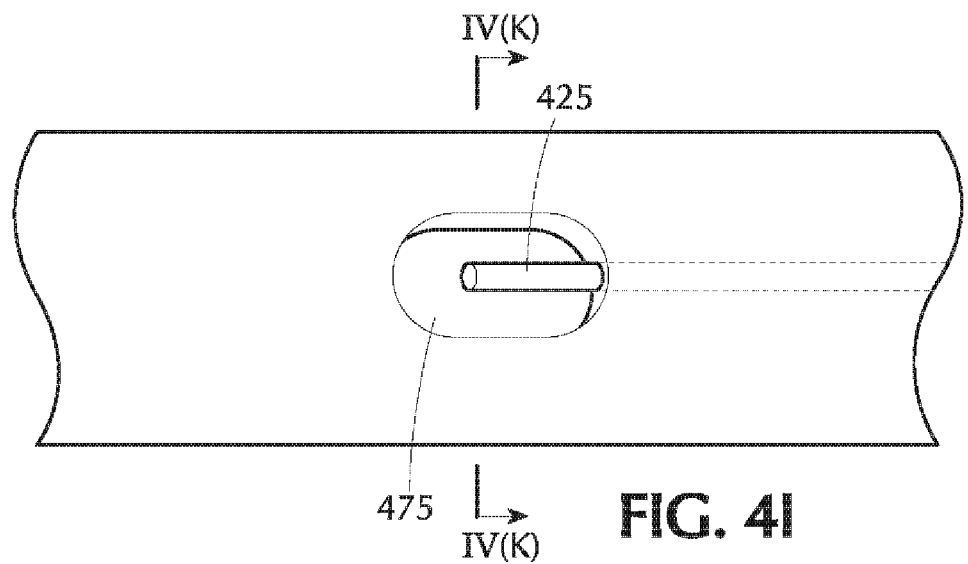
FIG. 4I is a partial top view of an axial section of the catheter shaft without the balloon, wherein the localized fluid communication channel is a punched hole (e.g., oval, circle, etc.) and the inflation lumen extends axially partially into the punched hole.
Figure 4J:
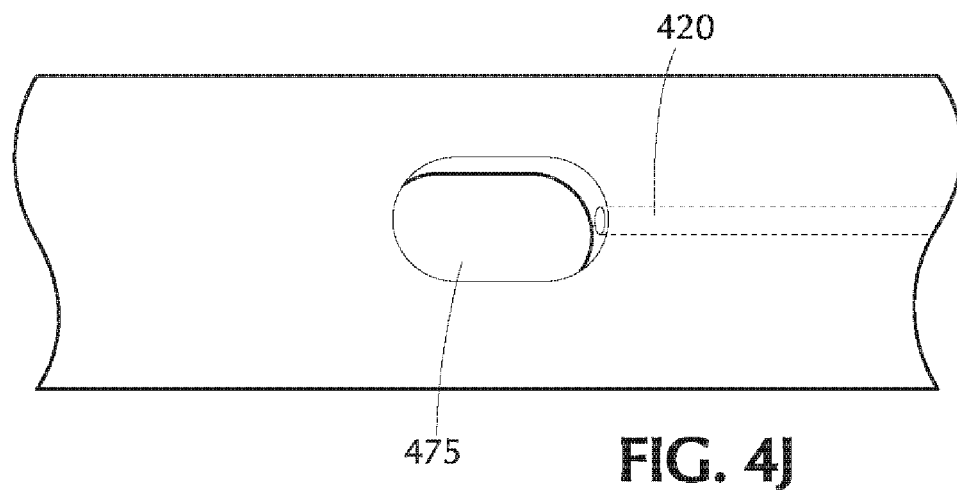
FIG. 4J is a partial top view of an axial section of the catheter shaft without the balloon, wherein the localized fluid communication channel is a punched hole (e.g., oval, circle, etc.) and the inflation lumen terminates at the interface with the punched hole.
Figure 4L:
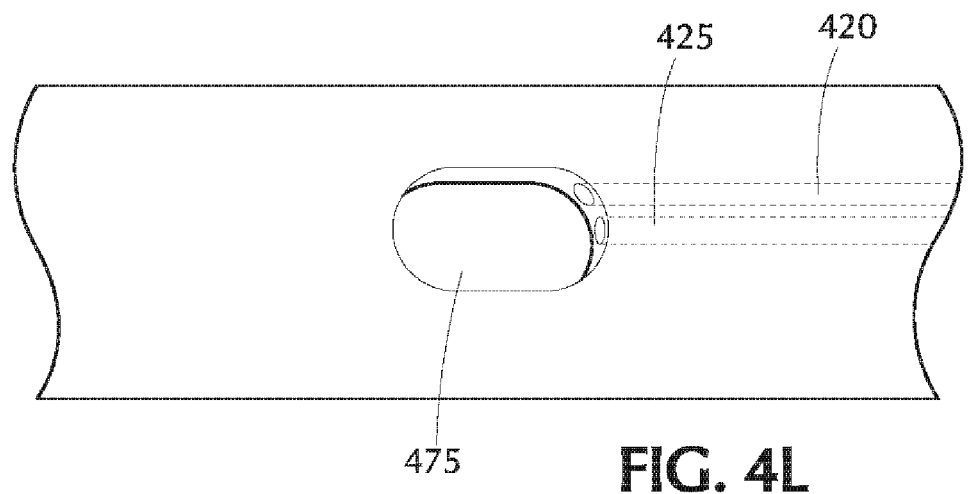
FIG. 4L is a partial top view of an axial section of the catheter shaft without the balloon, wherein the localized fluid communication channel is a punched hole (e.g., oval, circle, etc.) and respective terminating ends of the inflation and exhaust lumen terminate at the interface with the punched hole.

A top view of a section of the catheter shaft (without the balloon) shown in FIGS. 4I & 4J shows a first localized fluid communication channel as a punched hole (e.g., oval, circle, etc.) defined in an outer surface of the catheter shaft. The terminating distal end of the inflation lumen 425 extends partially into the punched hole 475 in FIG. 4I, whereas in FIG. 4J the terminating distal end of the inflation lumen 425 is aligned with the interface of the punched hole 475, that is, the terminating distal end of the inflation lumen does not extend into the punched hole. A radial cross-sectional view through the first localized fluid communication channel 475 of FIG. 4I along lines IV(K)-IV(K) is shown in FIG. 4K. The position of the inflation lumen 425 within the first localized fluid communication channel 475 in FIG. 4K is to the left; however, the position may be selected, as desired, anywhere within the first localized fluid communication channel 475 (e.g., midway within the channel, to the right within the channel, etc.). As previously mentioned, terminating distal ends of respective inflation and exhaust lumens may be aligned with (coincide with) an interface of a single punched hole defined in the outer surface of the catheter shaft serving as the single localized fluid communication channel, as shown in FIG. 4L.

FIG. 5 shows the present inventive balloon catheter 500 with the balloon 515 in an inflated state at a target site in an artery 550. Syringe 536 or other injection device is connected to the inflation port 535 in FIG. 5 to introduce inflation medium (e.g., 50/50 contrast/saline solution) into the inflation lumen. A one-way or manual valve 545 is connected to the exhaust port 537 to control the purging of residual air from the catheter. The main/guidewire port or opening 540 is also provided in the hub 530 for receiving a guidewire 90 therein.

Figure 6A:
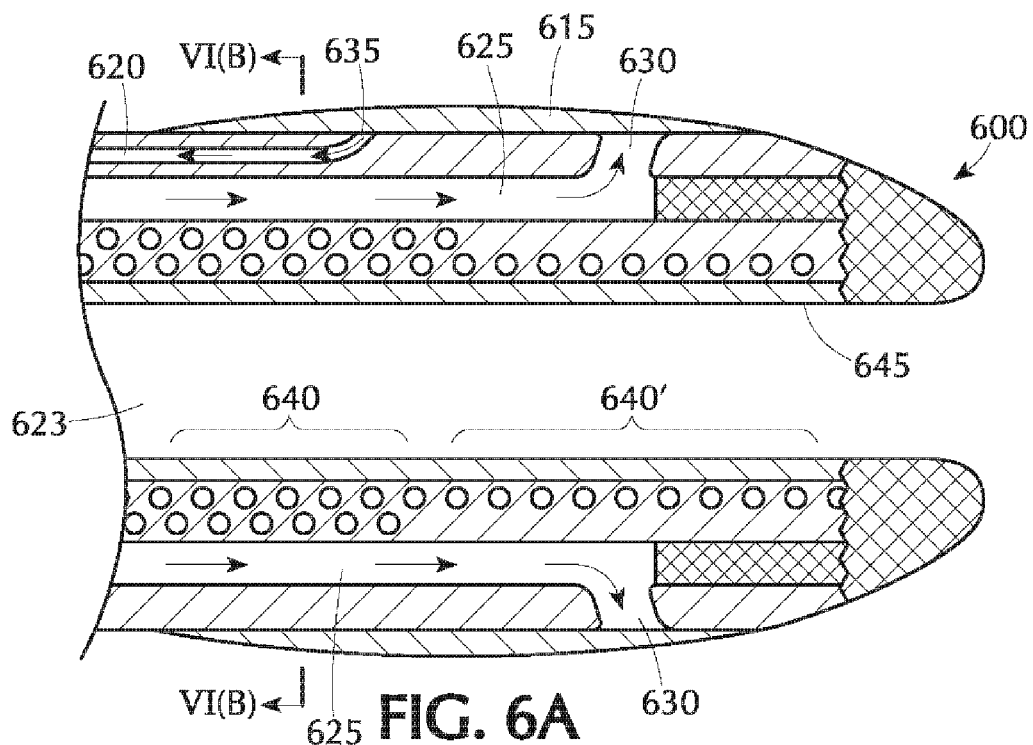
FIG. 6A is a partial axial cross-sectional view of the distal end of an exemplary configuration of the present inventive balloon catheter in a deflated state (non-inflated state); wherein the inflation lumen is concentrically arranged and the exhaust lumen is eccentrically arranged relative to that of the main/guidewire lumen.

FIG. 6A is a partial axial cross-sectional view of the distal end of another exemplary configuration of a balloon catheter 600 in accordance with the present invention, wherein the balloon 615 is in a deflated (non-inflated) state. The inflation and exhaust lumens 625, 620, respectively, are two separate channels or passageways that extend side-by-side axially in the catheter shaft or body. The inflation lumen 625 terminates in at least one inlet port, opening or channel 630 (two being illustrated in FIG. 6A) defined in the outer surface anywhere along the catheter shaft and in fluid communication with the balloon 615 through which the inflation medium passes. Whereas, the residual air is exhausted through an outlet port, opening or channel 635 and into the exhaust lumen 620 defined in the catheter shaft. A reinforcing member, preferably a metal wire, preferably a 0.001"-0.003" stainless steel wire such as SS304 grade, made into a coil, braid or both may be provided along a portion of the catheter shaft between the main lumen 623 and the inflation lumen 625 to enhance the stiffness of the distal region of the catheter to aid during navigation of the vessel. The reinforcing member is preferably embedded in a soft, flexible polymeric material to prevent the catheter lumen from ovalling, prolapsing and kinking.

Figure 6C:
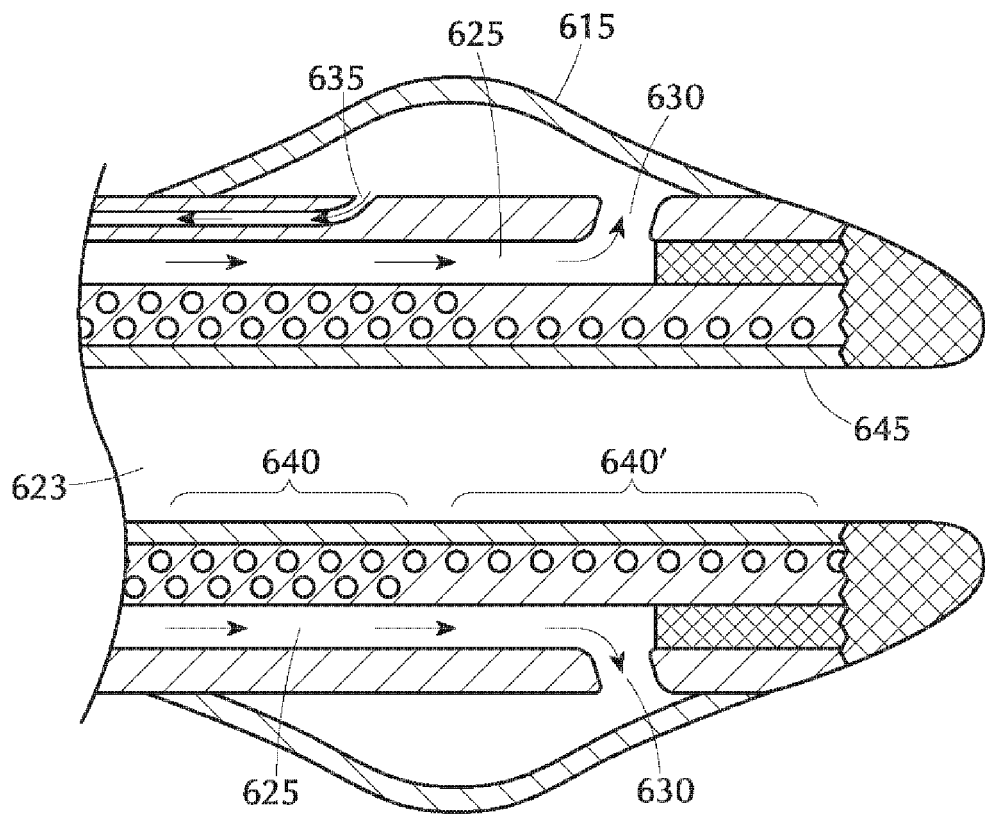
FIG. 6C is a partial axial cross-sectional view of the distal end of the balloon catheter of FIG. 6A, while the balloon is in an inflated state.
Figure 6B:
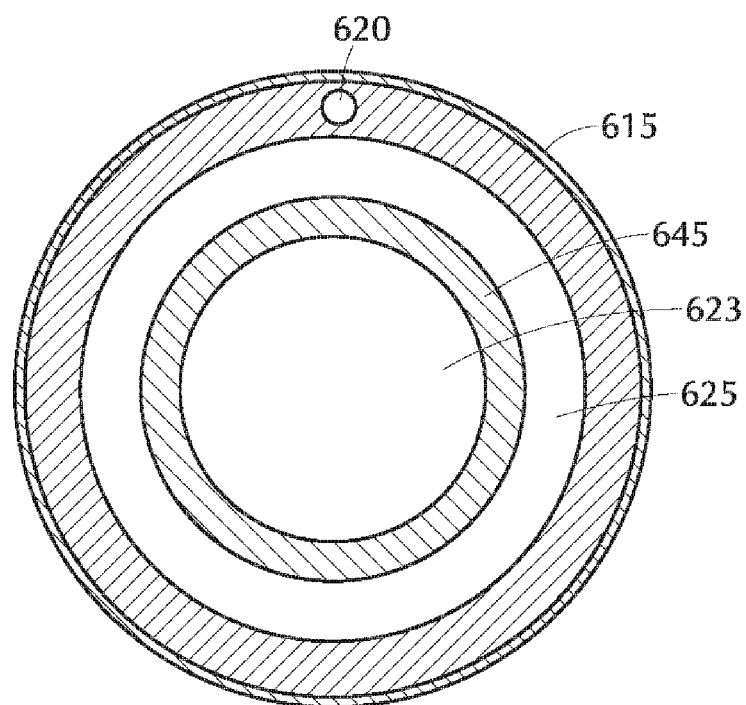
FIG. 6B is a radial cross-sectional view of the balloon catheter of FIG. 6A along lines VI(B)-VI(B)

In FIG. 6A the reinforcing member is a braid 640 disposed about a proximal region of the catheter shaft followed distally thereafter by a coil 640' disposed along a distal region of the catheter shaft. Alternatively, either the braid or coil alone may serve as the reinforcing member. To minimize friction when auxiliary devices are inserted through the main lumen, an inner liner, preferably made of polytetrafluoroethylene (PTFE), may be provided. Furthermore, to minimize kinking of the catheter in an axial direction during advancement through the vasculature, a reinforcing inner sheath or sleeve 645 may be provided between the main lumen 623 and the inflation lumen 625, radially inward of the reinforcing member. Preferably, inlet opening 630 is disposed distally in an axial direction relative to that of the outlet opening 635. As is illustrated in the radial cross-sectional view of FIG. 6B, the inflation lumen 625 is concentrically (coaxially) arranged, while the exhaust lumen 620 is eccentrically arranged, relative to the main lumen 623. FIG. 6C depicts the catheter 600 while the balloon 615 is in an inflated state with the inlet and outlet openings 630, 635, respectively, in fluid communication with the balloon 615. A top view (FIG. 6D) of the catheter shaft without the balloon shows the arrangement of the inlet and outlet openings 630, 635. Once again, any number of one or more inlet ports and one or more outlet ports may be varied, as desired, along with the arrangement of those ports along the catheter shaft.

Figure 7B:
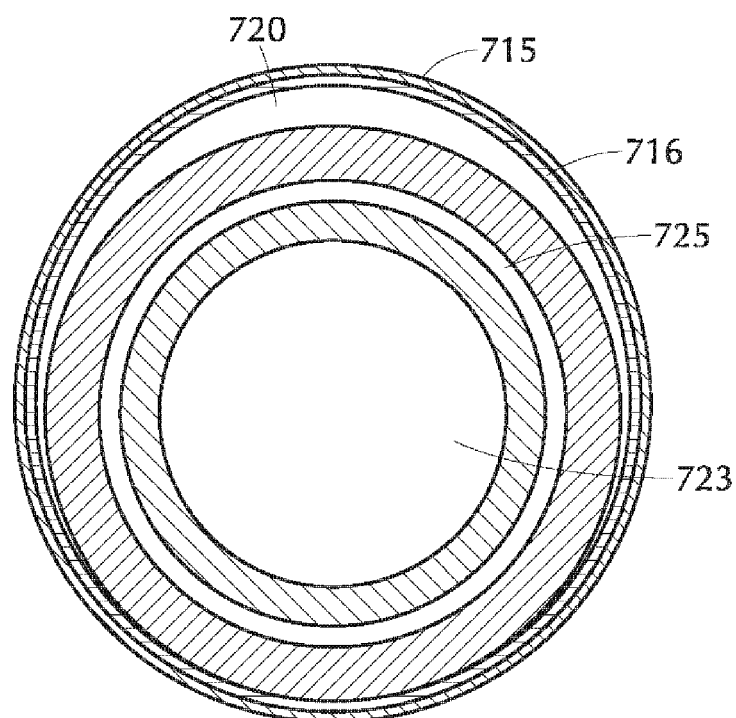
FIG. 7B is a radial cross-sectional view of the balloon catheter of FIG. 7A along lines VIIB-VIIB.
Figure 7A:
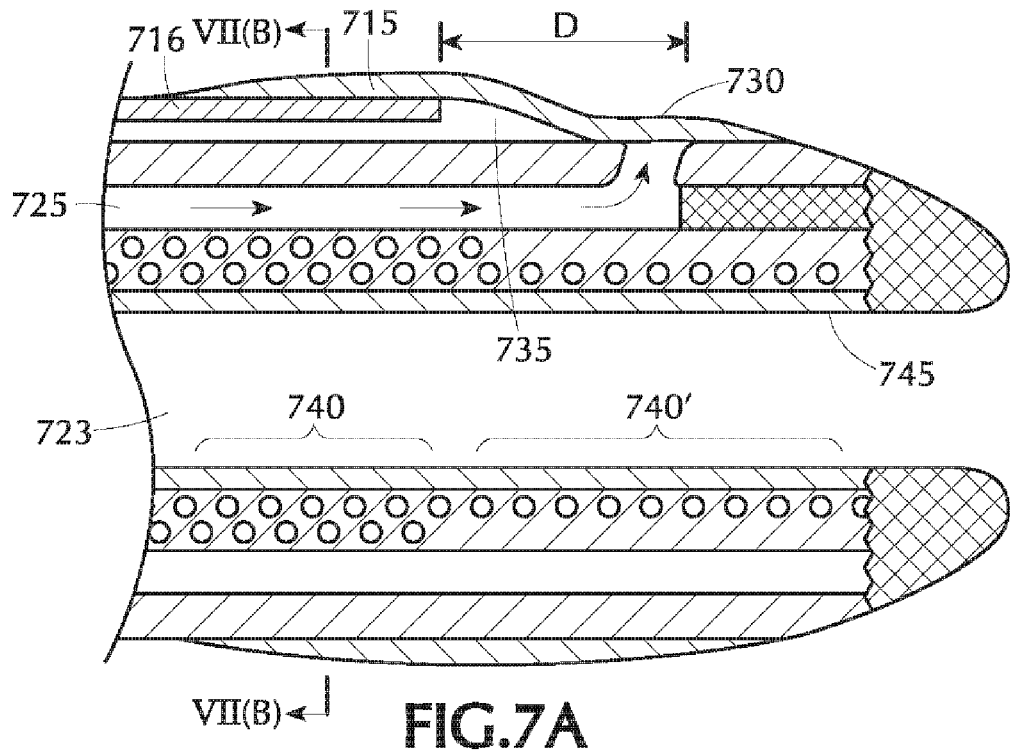
FIG. 7A is a partial axial cross-sectional view of the distal end of another exemplary configuration of the present inventive balloon catheter with the balloon in a deflated (non-inflated) state; wherein the inflation lumen is concentrically arranged and the exhaust lumen is eccentrically arranged relative to that of the main/guidewire lumen.
Figure 7C:
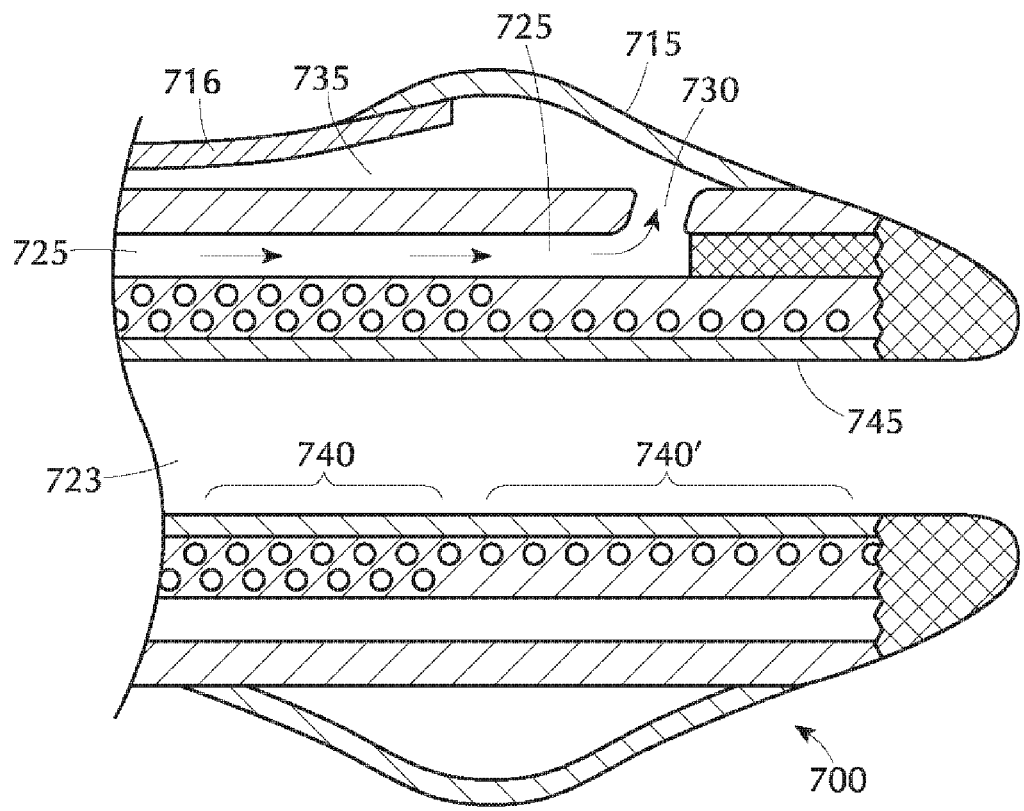
FIG. 7C is a partial axial cross-sectional view of the distal end of the balloon catheter of FIG. 7A, while the balloon is in an inflated state.

FIG. 7A is a partial longitudinal cross-sectional view of the distal end of yet another exemplary configuration of the balloon catheter 700 in accordance with the present invention. Once again, the inflation lumen 725 is disposed radially outward of the main lumen 723 between the concentric shafts (see FIG. 7B). An exhaust lumen 720 is created by bonding, welding, mounting or attaching a thin polymer jacket 716 about the outer surface of the catheter shaft creating a passageway or space therebetween that serves as an exhaust lumen 720. Inflation medium travels though the inflation lumen 725, out from the inlet opening 730, and into the balloon 715. Residual air travels along the outer surface of the catheter shaft enters the outlet opening 735 and through the exhaust lumen 720 created by the polymer jacket 716 mounted to the outer surface of the catheter shaft. The axial distance D between the inlet port 730 and the outlet port 735 is preferably minimized to assist in communication of expelled residual air between the inflation and exhaust lumen. The relatively large exhaust lumen created by the relatively thin polymer jacket mounted to the outer surface of the outer shaft provides the benefit of reduced prepping time and superior deflation times when the exhaust lumen is opened. As with the previously described configurations, reinforcing structures, e.g., a braid 740, coil 740' and/or inner sheath 745 may be employed to provide enhanced stiffness to the catheter.

Figure 8A:
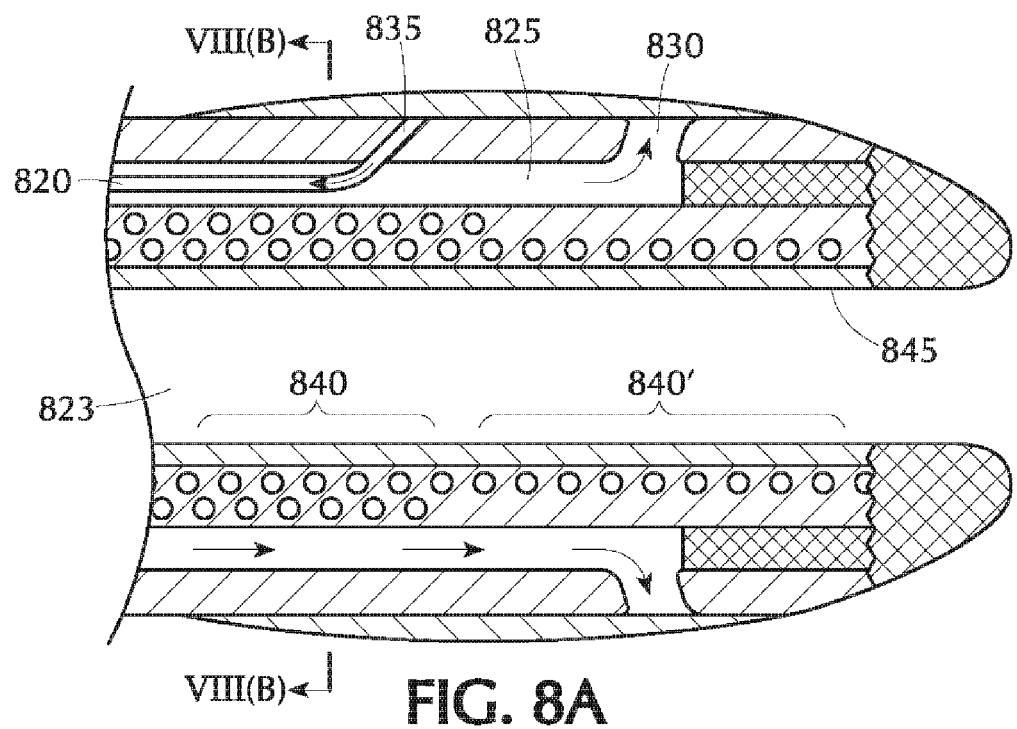
FIG. 8A is a partial axial cross-sectional view of the distal end of still another exemplary configuration of the present inventive balloon catheter with the balloon in a deflated (non-inflated) state; wherein the inflation lumen is concentrically arranged and the exhaust lumen is eccentrically arranged relative to that of the main/guidewire lumen; and wherein the exhaust lumen is disposed within and extends axially through a portion of the inflation lumen.
Figure 8C:
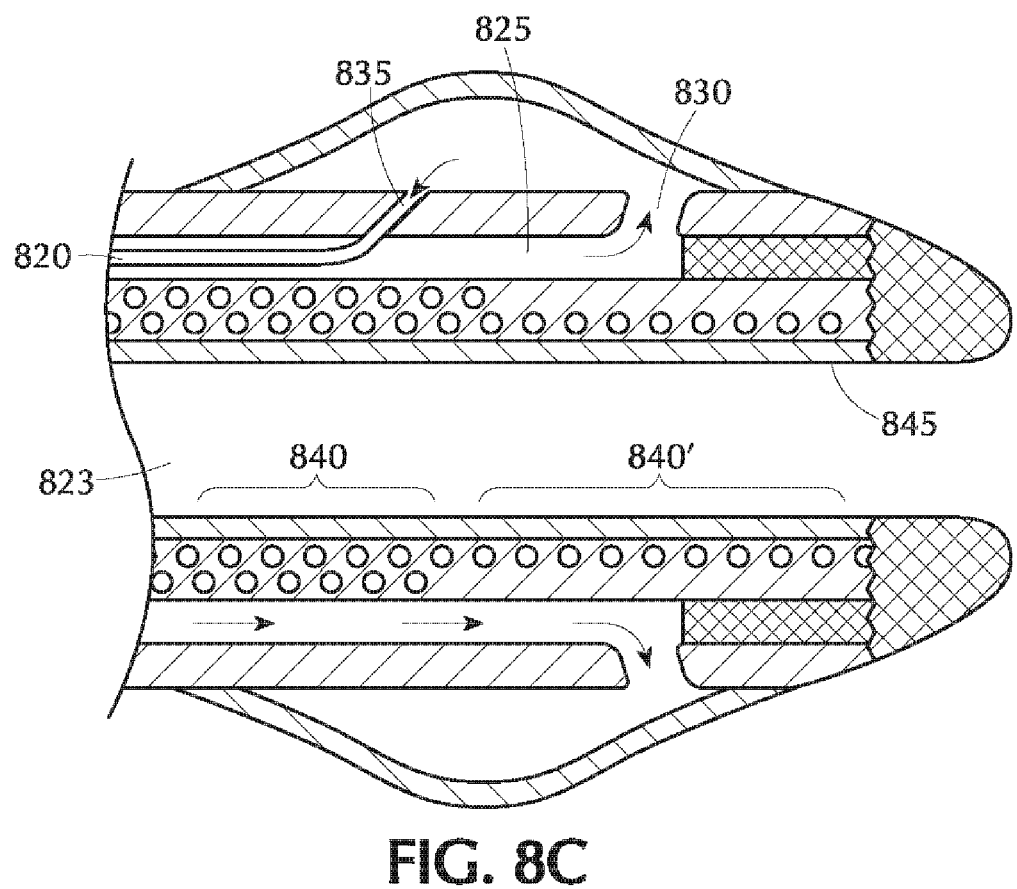
FIG. 8C is a partial axial cross-sectional view of the distal end of the balloon catheter of FIG. 8A, while the balloon is in an inflated state.
Figure 8B:
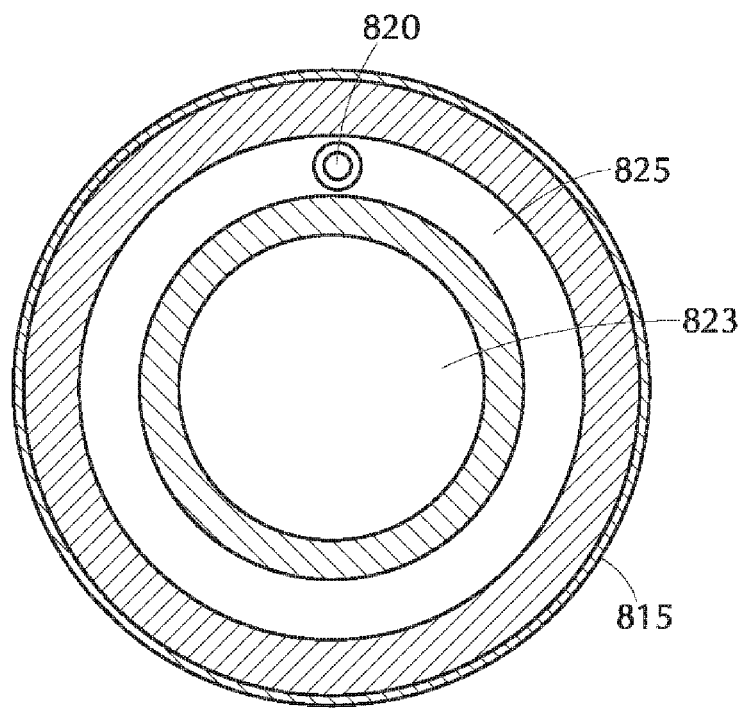
FIG. 8B is a radial cross-sectional view of the balloon catheter of FIG. 8A along lines VIII(B)-VIII(B)

FIG. 8A is a partial axial cross-sectional view of the distal end of still another exemplary configuration of the balloon catheter 800 in accordance with the present invention. This design is similar to that of FIG. 6A in that the inflation lumen 825 is concentrically arranged relative to the main lumen 823. However, the axially extending exhaust lumen 820 is an independent isolated lumen disposed entirely within the inflation lumen 825 between the inner and outer shafts of the catheter body, as shown in FIG. 8B. Once again, the inlet opening 830 is in fluid communication with the balloon 815, while the outlet opening 835 is defined in the outer shaft providing a direct communication between the balloon 815 and exhaust lumen 820. An enlarged inner diameter is a benefit of this balloon catheter design able to accommodate a wide range of ancillary devices having larger outer diameters. As with all the different configuration, reinforcing structures, e.g., a braid 840, a coil 840' and/or an inner sheath 845 may be employed to provide enhanced stiffness to the catheter.

Figure 9B:
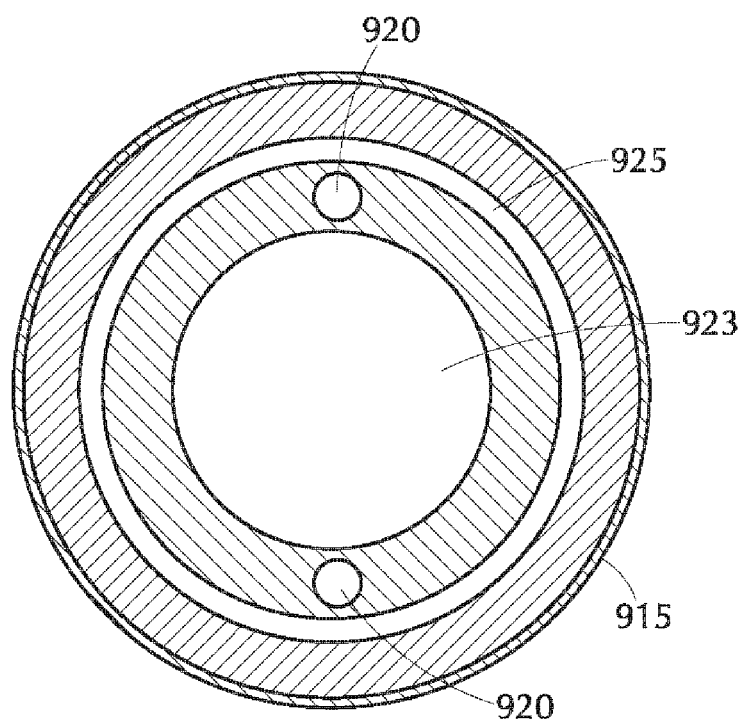
FIG. 9B is a radial cross-sectional view of the balloon catheter of FIG. 9A along lines IX(B)-IX(B)
Figure 9A:
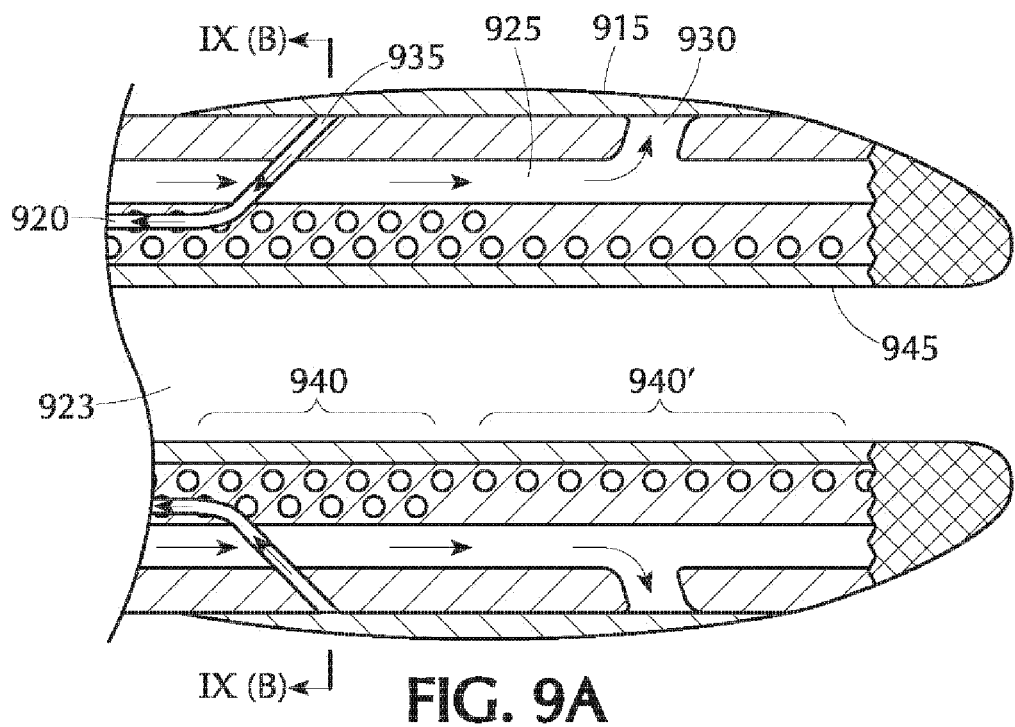
FIG. 9A is a partial axial cross-sectional view of the distal end of yet another exemplary configuration of the present inventive balloon catheter with the balloon in a deflated (non-inflated) state; wherein the inflation lumen is concentrically arranged and the two exhaust lumens are eccentrically arranged relative to that of the main/guide lumen; and wherein the exhaust lumen crosses over that of the inflation lumen radially inward of the exhaust lumen.
Figure 9C:
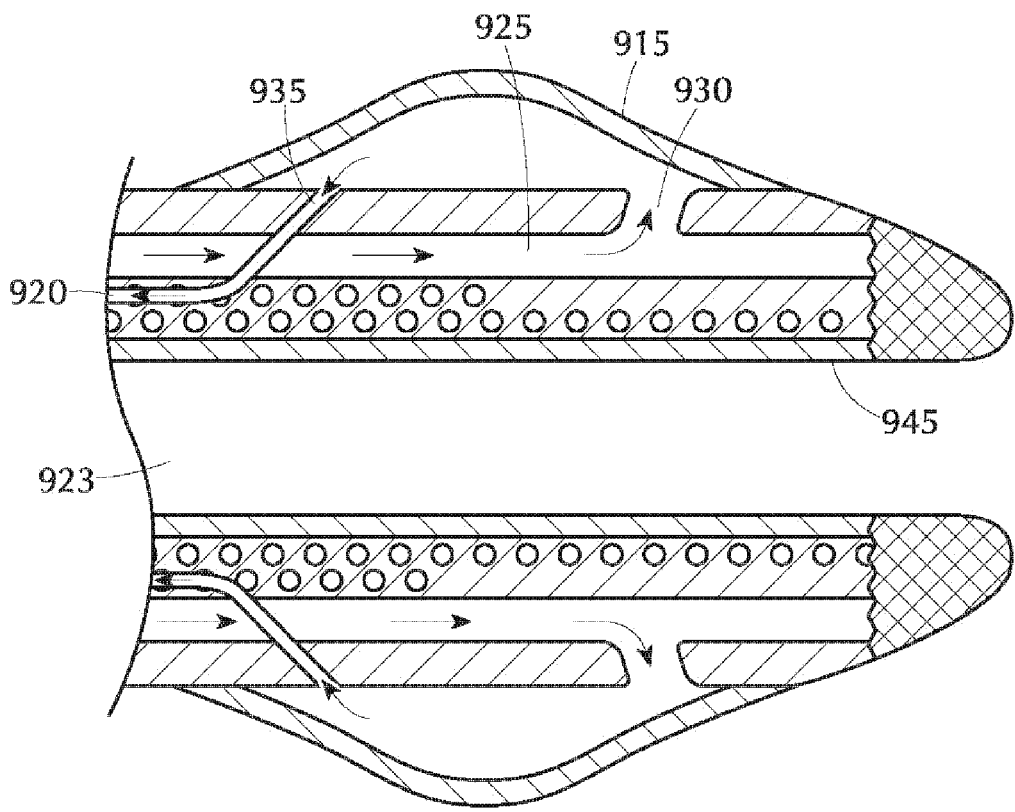
FIG. 9C is a partial axial cross-sectional view of the distal end of the balloon catheter of FIG. 9A, while the balloon is in an inflated state.

Yet another exemplary configuration of the balloon catheter 900 in accordance with the present invention is represented by the partial axial cross-sectional view of the distal end of the catheter in FIG. 9A. The inflation lumen 925 is concentrically arranged relative to the main lumen 923, while each of the two exhaust lumens 920 are eccentrically arranged relative to the main lumen 923. In the previous embodiments (FIGS. 6A, 6B, 7A & 7B), the inflation lumen was disposed between the inner and outer shafts comprising the catheter body. In the design of FIG. 9A, the exhaust lumen 920 is disposed within the inner catheter shaft radially between the main lumen 923 and the inflation lumen 925. As is evident from the longitudinal cross-sectional view in FIG. 9B, the exhaust lumen 920 traverses (cross-over without being in fluid communication) the inflation lumen 925. FIG. 9B is a radial cross-sectional view of the catheter along lines IX(B)-IX(B) in which the two exhaust lumens 920 disposed within the inner shaft and radially inward of the inflation lumen 925 is clearly illustrated. FIG. 9C depicts the catheter of FIG. 9A while in an inflated state.

In each of the different exemplary configurations illustrated in FIGS. 6B, 7B, 8B, 9B, the inflation lumen is concentric (coaxial), while the exhaust lumen is eccentric, with respect to the main/guidewire lumen.

Figures 10A, 10B:
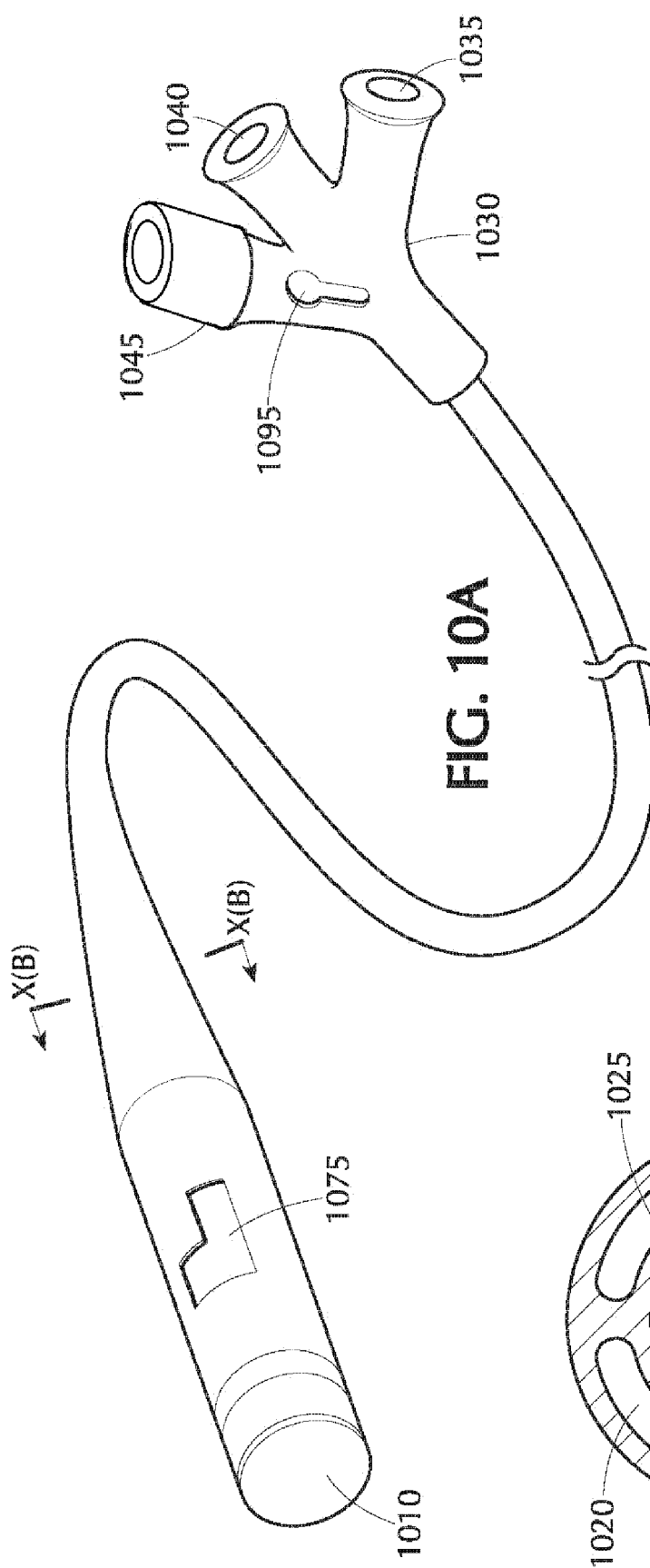
FIG. 10A is a perspective view of still another aspect of the present inventive balloon guide catheter without the balloon.
FIG. 10B is a radial cross-sectional view of the balloon guide catheter of FIG. 10A along lines X(B)-X(B)

FIG. 10A is a perspective view of yet another configuration of the present inventive balloon guide catheter having dual lumen (one inflation lumen 1025 and one exhaust lumen 1020) defined in the outer wall of the catheter shaft, aside from the main lumen 1023. Terminating distal ends of the respective inflation and exhaust lumens 1025, 1023 coincide with a localized fluid communication channel, recess or basin 1075. The localized fluid communication channel 1075 is where the terminating distal ends of the respective inflation and exhaust lumens are in fluid communication with one another. A balloon, not illustrated in FIG. 10A, is assembled taut or snug about the outer surface of the distal region of the catheter shaft covering the localized fluid communication channel 1075. The side-by-side axial arrangement of the radial section inflation and exhaust lumens 1025, 1020 disposed in the outer wall of the outer shaft radially outward from the main lumen 1023 is shown in FIG. 10B. Different arrangements of the one or more inflation lumen and one or more exhaust lumen are possible, such as, but not limited to, those depicted in FIGS. 3A-3D. A proximal hub 1030 is connected to the proximal end of the balloon guide catheter. Hub 1030 includes a main/guidewire port 1040, an inflation port 1035 and an exhaust/vent port 1045. A valve 1095 is disposed at the exhaust port 1045.

Figure 11A:
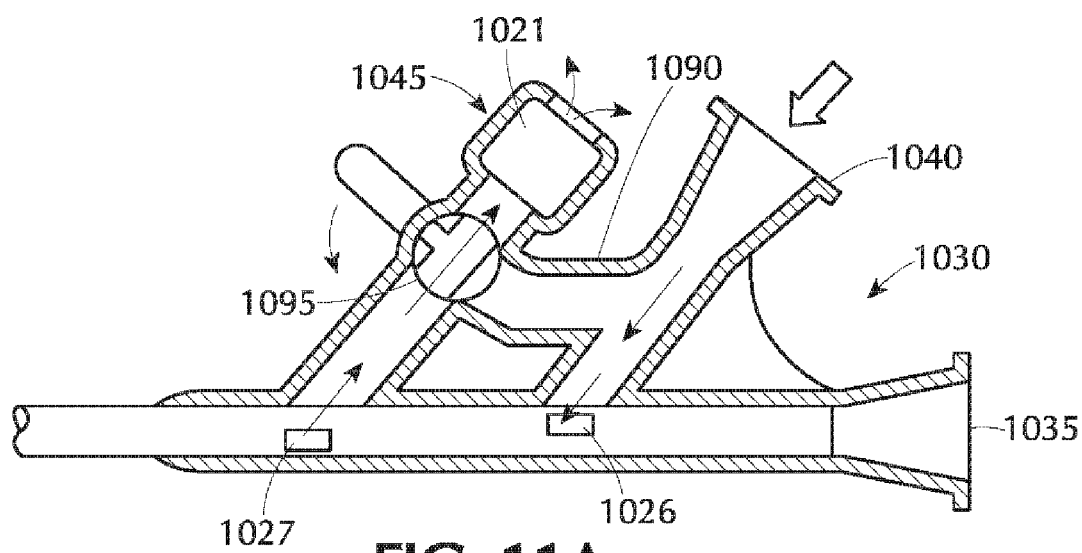
FIG. 11A is an axial cross-sectional view of the hub in FIG. 10A when the valve is positioned in an open state during purging of the residual air from the catheter as well as inflation of the balloon.
Figure 11B:
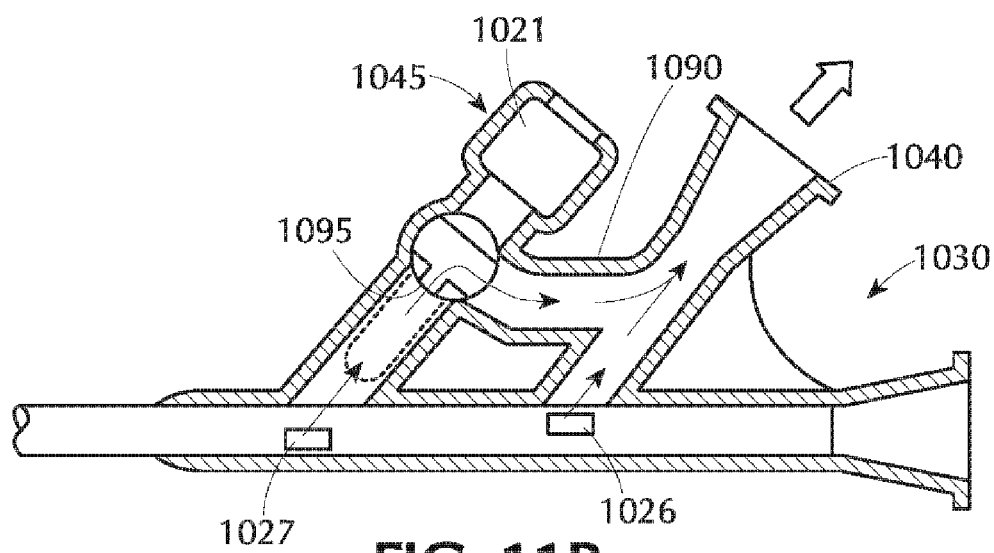
FIG. 11B is an axial cross-sectional view of the hub in FIG. 10A when the valve is positioned in a closed state during deflation of the balloon.

FIG. 11A is a cross-sectional axial view of the hub 1030 in FIG. 10A, wherein a 3-way valve 1095 is oriented or positioned for inflation of the balloon with an inflation medium (e.g., 50/50 contrast/saline solution) injected into the inflation port 1040 (via a syringe 536 similar to that shown in FIG. 5). Inflation medium injected into the inflation port 1040 enters an inflation opening 1026 in the outer wall of the catheter shaft and fills the inflation lumen 1025. Upon the inflation medium reaching the localized fluid communication channel it enters the exhaust lumen 1020 and travels proximally therethrough exiting from the vent opening 1027 and into the hub 1030. As the inflation medium is dispensed from the syringe under pressure and travels through the catheter residual air from within the inflation lumen and balloon is vented, purged or exhausted proximally from the catheter. Valve 1095 disposed distally of the exhaust port 1045 is oriented or positioned in FIG. 11A in an open state allowing the flow of residual air therethrough which then passes out of the exhaust port 1045 via a microporous membrane or filter 1021. Pores or openings of the microporous membrane or filter 1021 are sized to permit the passage therethrough of residual air, while prohibiting or preventing passage therethrough of the inflation medium. Once the residual air has been fully purged from the catheter, any additional flow of the inflation medium or increase in pressure applied by the syringe causes the balloon to inflate. Flow rates of the inflation medium are maintained so that full venting of residual air occurs without sufficient pressure built-up or generated in the catheter to initiate inflation of the balloon.

The localized fluid communication channel 1075 underneath the balloon is designed so that both lumens (the exhaust lumen 1020 and the inflation lumen 1025) communicate allowing residual air and inflation medium to flow out from the terminating distal end of the inflation lumen and into the terminating distal end of the exhaust lumen.

Deflation of the balloon is achieved by attaching a vacuum (e.g., syringe) to the inflation port 1040 creating a negative pressure within the catheter. When it is time to deflate the balloon, valve 1095 is oriented to close off flow to the exhaust port 1045. Upon application of a vacuum or suction (e.g., syringe) attached to the inflation port 1040 creating a negative pressure within the catheter the inflation medium exhausted from the exhaust lumen is redirected into the bridge fluid communication channel 1090, combining with the inflation medium vented through the inflation lumen and out from the inflation port 1040. This unique hub configuration and, in particular, the orientation or positioning of the valve during deflation to close off the exhaust port 1045, upon application of a vacuum to the inflation port provides for the removal of inflation medium simultaneously through both inflation and exhaust lumens thereby optimizing deflation of the balloon.

Preferably, the configuration of the hub 1030 is optimized by minimizing its overall axial length in order to minimize cost of manufacture as well as minimize the unusable length of hub that other catheters go through. It is also contemplated to replace the 3-way manual valve 1095 with a spring-loaded or ball valve that is automatically actuated upon the introduction of a suction or vacuum applied to the inflation port 1040.

Exhausting of residual air from the present inventive balloon catheter is less complicated requiring less time to accomplish than conventional devices. In accordance with the present invention, air is automatically purged in the proximal direction from the balloon catheter. Specifically, preparation of the present inventive balloon catheter starts with inflation medium being passed through the inflation lumen which coincides with the residual air being purged, evacuated or exhausted from the system in a proximal direction via the exhaust lumen reducing preparation time. Furthermore, since the residual air is vented in a proximal direction safety concerns associated with purging air once the catheter has been introduced in the body have been eliminated.

The present inventive closed loop proximal venting system has several advantages. Since the residual air is vented in a proximal direction preparation of the device by the interventionalist may occur while the device is in the patient. Another benefit of the present inventive closed loop proximal design is that the inflation medium automatically expels the residual air/gas through the microporous membrane and out the exhaust lumen while the inflation medium is prevented from passing through the microporous membrane thereby causing the balloon to inflate and expand. Accordingly, the need for a valve or other mechanical device for causing the balloon to inflate once the residual air has been purged has been eliminated in accordance with the present invention.

Thus, while there have been shown, described, and pointed out fundamental novel features of the invention as applied to a preferred embodiment thereof, it will be understood that various omissions, substitutions, and changes in the form and details of the systems/devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A balloon guide catheter system comprising:
   a balloon guide catheter, comprising:
   a catheter shaft with a proximal end and an opposite distal end; wherein the catheter shaft includes: (i) a main lumen defined axially through the catheter shaft; (ii) an inflation lumen extending axially along the catheter shaft; the inflation lumen having a proximal end, an opposite terminating distal end; and (iii) an exhaust lumen extending axially along the catheter shaft, the exhaust lumen having a proximal end and an opposite terminating distal end;
   a balloon disposed about a distal region of an outer surface of the catheter shaft; wherein the terminating distal end of the inflation lumen and the terminating distal end of the exhaust lumen are in localized fluid communication with one another underneath the balloon when the balloon is in a non-inflated state held taut against the outer surface of the catheter shaft from a proximal end to an opposite distal end of the balloon; and
   wherein the exhaust lumen is configured to purge residual air in a proximal direction and out from a proximal region of the balloon guide catheter;
   wherein the outer surface of the catheter shaft has a first localized fluid communication channel defined therein located underneath the balloon via which the terminating distal ends of the respective inflation and exhaust lumens are in localized fluid communication with one another; wherein the first localized fluid communication channel defined in the outer surface of the catheter shaft ensures that in response to injection of inflation medium via the inflation lumen the residual air passes through the exhaust lumen and the balloon is maintained in the non-inflated state held taut against the outer surface of the catheter shaft without inflating the balloon.

2. The balloon guide catheter system according to claim 1, wherein the inflation and exhaust lumens are radially separated a predetermined distance from one another.

3. The balloon guide catheter system according to claim 1, wherein the exhaust lumen is disposed within the inflation lumen.

4. The balloon guide catheter system according to claim 1, wherein the exhaust lumen is eccentrically arranged relative to the main lumen.

5. The balloon guide catheter system according to claim 4, wherein the exhaust lumen is disposed radially inward of, radially outward of, or within the inflation lumen.

6. The balloon guide catheter system according to claim 1, further comprising a single hub connected to the proximal end of the catheter shaft; the single hub comprising:
   an inflation port in fluid communication with the inflation lumen;
   an exhaust port in fluid communication with the exhaust lumen;
   a bridge fluid communication channel connecting the inflation and exhaust ports;
   a membrane disposed within the exhaust port, the membrane having openings defined therein sized to permit passage of only the residual air therethrough;
   a valve disposed within the exhaust port distally of the membrane, the valve being transitionable between only two states: (i) an open state in which the residual air is permitted to pass through the membrane and out from the exhaust port; and (ii) a closed state in which inflation medium from the exhaust lumen is redirected through the bridge fluid communication channel and into the inflation lumen.

7. The balloon guide catheter system according to claim 6, wherein irrespective of the state of the valve, the residual air via the exhaust lumen of the catheter shaft is permitted to exit from the balloon guide catheter system.

8. The balloon guide catheter system according to claim 6, wherein the catheter shaft has an outer wall with an inflation opening defined therein in fluid communication with the inflation port and a vent opening defined therein in fluid communication with the exhaust port and arranged distally relative to the inflation opening.

9. A method for using a balloon guide catheter system including a balloon guide catheter having a catheter shaft with a proximal end and an opposite distal end; wherein the catheter shaft includes: (i) a main lumen defined axially through the catheter shaft; (ii) an inflation lumen extending axially along the catheter shaft, the inflation lumen having a proximal end, an opposite terminating distal end and being disposed radially outward and concentric with respect to the main lumen; (iii) an exhaust lumen extending axially along the catheter shaft, the exhaust lumen having a proximal end and an opposite terminating distal end; the balloon guide catheter further including a balloon disposed about a distal region of an outer surface of the catheter shaft; wherein the terminating distal end of the inflation lumen and the terminating distal end of the exhaust lumen are in fluid communication with one another underneath the balloon when the balloon is in a non-inflated state held taut against the outer surface of the catheter shaft from a proximal end to an opposite distal end of the balloon; the exhaust lumen configured to purge residual air in a proximal direction and out from a proximal region of the balloon guide catheter; wherein the outer surface of the catheter shaft has a first localized fluid communication channel defined therein located underneath the balloon via which the terminating distal ends of the respective inflation and exhaust lumens are in localized fluid communication with one another; wherein the first localized fluid communication channel defined in the outer surface of the catheter shaft ensures that in response to injection of inflation medium via the inflation lumen the residual air passes through the exhaust lumen and the balloon is maintained in the non-inflated state held taut against the outer surface of the catheter shaft without inflating the balloon; the method comprising the steps of:
   advancing the balloon guide catheter to a target site within a vessel;
   dispensing an inflation medium through an inflation port of a single hub connected to the proximal end of the catheter shaft and into the inflation lumen only after advancing the balloon guide catheter to the target site within the vessel;

advancing distally through the inflation lumen the residual air pushed by the dispensed inflation medium;

exhausting proximally through the exhaust lumen the residual air exiting from the terminating distal end of the inflation lumen; and expelling the residual air through a membrane permitting passage therethrough of only the residual air and out from the proximal region of the balloon guide catheter.

10. The method according to claim 9, wherein the expelling step comprises positioning a valve in an open state to allow the passage of the residual air therethrough and out of the single hub via an exhaust port.

11. The method according to claim 10, further comprising the step of:

following fully purging of the residual air from the balloon guide catheter, inflating of the balloon to an inflated state by the continued dispensing of the inflation medium into the inflation lumen.

\* \* \* \* \*